(12) United States Patent
Gonnelli et al.

(10) Patent No.: US 9,968,731 B2
(45) Date of Patent: *May 15, 2018

(54) FLUID DELIVERY DEVICE

(71) Applicant: Valeritas, Inc., Bridgewater, NJ (US)

(72) Inventors: Robert R. Gonnelli, Mahwah, NJ (US); Steven F. Levesque, North Pembroke, MA (US)

(73) Assignee: VALERITAS, INC., Bridgewater, NJ (US)

( * ) Notice: Subject to any disclaimer, the term of this patent is extended or adjusted under 35 U.S.C. 154(b) by 248 days.

This patent is subject to a terminal disclaimer.

(21) Appl. No.: 14/790,044

(22) Filed: Jul. 2, 2015

(65) Prior Publication Data

US 2015/0306306 A1 Oct. 29, 2015

Related U.S. Application Data

(63) Continuation of application No. 13/500,136, filed as application No. PCT/US2010/052352 on Oct. 12, 2010, now Pat. No. 9,101,706.

(Continued)

(51) Int. Cl.
*A61M 5/142* (2006.01)
*A61M 5/162* (2006.01)
(Continued)

(52) U.S. Cl.
CPC ...... *A61M 5/14248* (2013.01); *A61M 5/1454* (2013.01); *A61M 5/14526* (2013.01);
(Continued)

(58) Field of Classification Search
CPC ......... A61M 2005/14252; A61M 2005/14506; A61M 2202/0007; A61M 5/14248;
(Continued)

(56) References Cited

U.S. PATENT DOCUMENTS

| 4,194,505 A | 3/1980 | Schmitz |
| 4,437,859 A | 3/1984 | Whitehouse et al. |

(Continued)

FOREIGN PATENT DOCUMENTS

| CA | 101460216 A | 6/2009 |
| CN | 1671430 A | 9/2005 |

(Continued)

OTHER PUBLICATIONS

Second Office Action dated Mar. 21, 2017 for Chinese Patent Application No. 201410634901.6.

(Continued)

*Primary Examiner* — Quynh-Nhu H Vu
(74) *Attorney, Agent, or Firm* — Morgan, Lewis & Bockius LLP

(57) ABSTRACT

A fluid delivery device comprises a housing having a fluid reservoir. A needle is in fluid communication with the fluid reservoir in an engaged position and out of fluid communication with the fluid reservoir in armed and storage positions. A proximal end of a biasing member is coupled to the housing and a distal end of the biasing member is configured to deliver a force to the fluid reservoir. A piston member extends through the biasing member and is coupled to the distal end of the biasing member. The piston member is fixed with respect to the housing in a locked position such that the biasing member does not deliver the force to the fluid reservoir and moveable with respect to the housing in a released position such that the biasing member delivers the force to the fluid reservoir. Transitioning the needle from the storage position to the armed position transitions the piston from the locked position to the released position.

10 Claims, 22 Drawing Sheets

Related U.S. Application Data

(60) Provisional application No. 61/325,136, filed on Apr. 16, 2010, provisional application No. 61/251,236, filed on Oct. 13, 2009.

(51) Int. Cl.
*A61M 5/168* (2006.01)
*A61M 5/145* (2006.01)

(52) U.S. Cl.
CPC ...... *A61M 5/1626* (2013.01); *A61M 5/16804* (2013.01); *A61M 5/14566* (2013.01); *A61M 2005/14252* (2013.01); *A61M 2005/14506* (2013.01); *A61M 2202/0007* (2013.01)

(58) Field of Classification Search
CPC ............ A61M 5/14526; A61M 5/1454; A61M 5/14566; A61M 5/1626; A61M 5/16804
See application file for complete search history.

(56) References Cited

U.S. PATENT DOCUMENTS

| | | | |
|---|---|---|---|
| 5,616,132 A | 4/1997 | Newman | |
| 5,858,001 A * | 1/1999 | Tsals | A61M 5/14248 604/135 |
| 6,641,566 B2 * | 11/2003 | Douglas | A61M 5/31511 604/135 |
| 9,101,706 B2 * | 8/2015 | Gonnelli | A61M 5/14248 |
| 2002/0123735 A1 | 9/2002 | Rake et al. | |
| 2002/0123740 A1 | 9/2002 | Flaherty et al. | |
| 2005/0033232 A1 | 2/2005 | Kriesel | |
| 2005/0119618 A1 | 6/2005 | Gonnelli | |
| 2005/0215850 A1 | 9/2005 | Klein et al. | |
| 2006/0186143 A1 | 8/2006 | Argentine | |
| 2006/0189939 A1 | 8/2006 | Gonnelli et al. | |
| 2006/0264835 A1 | 11/2006 | Nielsen et al. | |
| 2007/0203454 A1 | 8/2007 | Shermer et al. | |
| 2007/0219496 A1 | 9/2007 | Kamen et al. | |
| 2009/0240232 A1 * | 9/2009 | Gonnelli | A61M 5/14526 604/506 |

FOREIGN PATENT DOCUMENTS

| | | |
|---|---|---|
| CN | 101355979 A | 1/2009 |
| CN | 100479875 C | 4/2009 |
| CN | 102665799 B | 12/2014 |
| TW | 301503 B | 2/1986 |

OTHER PUBLICATIONS

Supplemental Search Report dated Dec. 17, 2014 for European Patent Application No. 10823957.
International search report and written opinion dated Dec. 10, 2010 from International Patent Application No. PCT/US2010/052353.
First Search Report dated Apr. 18, 2016 for Australian Patent Application No. 2015202656.

* cited by examiner

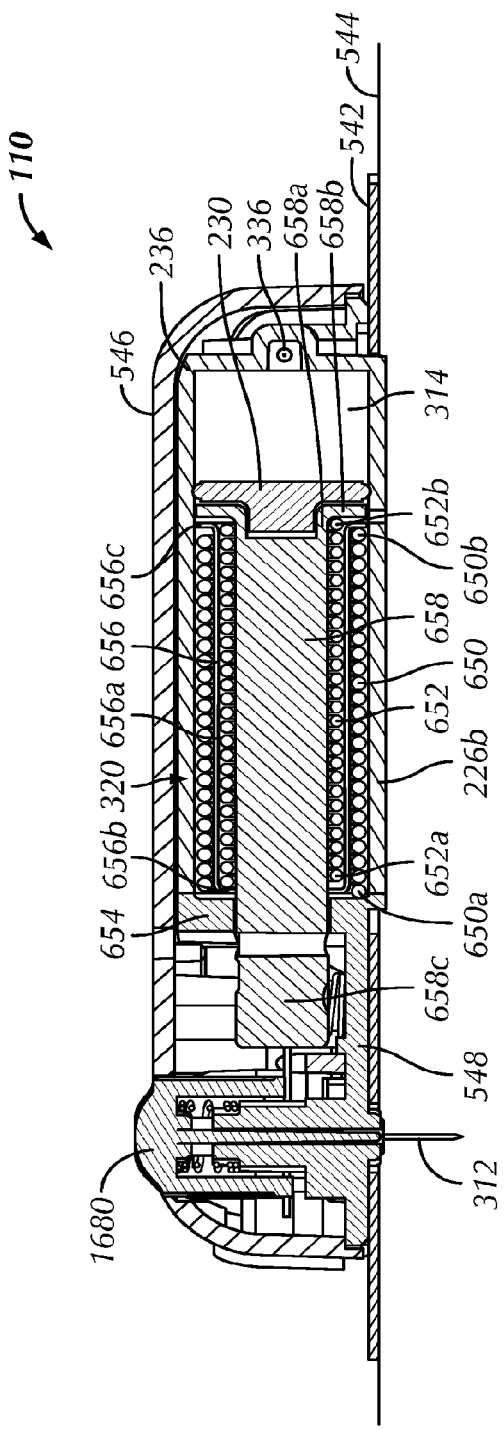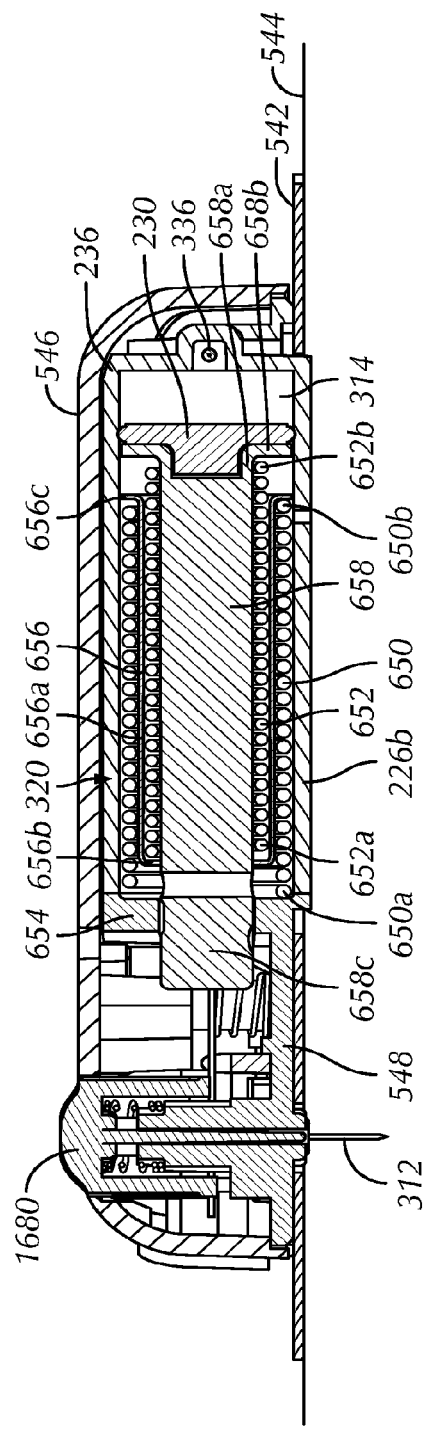
FIG. 6B
FIG. 6C

FLUID DELIVERY DEVICE

CROSS-REFERENCE TO RELATED APPLICATIONS

This application is a continuation of U.S. patent application Ser. No. 13/500,136, filed on Oct. 12, 2010, which is a National Stage Patent Application of International Patent Application No. PCT/US2010/052352 filed on Oct. 12, 2010, which claims the benefit of U.S. Provisional Patent Application No. 61/251,236 filed on Oct. 13, 2009 entitled "Fluid Delivery Device", and U.S. Provisional Patent Application No. 61/325,136 filed Apr. 16, 2010 entitled "Fluid Delivery Device" all of which are incorporated by reference herein in their entirety.

BACKGROUND OF THE INVENTION

The present invention generally relates to a fluid delivery device and more particularly to an ambulatory device for delivering a medicament to a patient.

Many attempts have been made to provide dosing of drugs and other fluids, such as insulin, using ambulatory pump systems. Although some systems for continuous delivery work quite well, individuals using these systems, particularly in continuous dose mode, need to monitor the devices closely to ensure continuity and accuracy of dosing under variable environmental conditions such as temperature and air pressure. In addition, there are few options for individuals who require the ability to vary the dose of medication quickly and accurately, and most of the available options are cumbersome, difficult to operate, intrusive, and/or expensive.

Accordingly, it would be desirable to provide a simple, intuitive, inexpensive ambulatory device able to provide fluid dosing under patient control, as well as safety and consistency in the metered and/or continuous dose over a wide range of environmental conditions.

BRIEF SUMMARY OF THE INVENTION

In one embodiment there is a fluid delivery device that comprises a housing having a fluid reservoir. A needle has a storage position, an armed position, and an engaged position. The needle is in fluid communication with the fluid reservoir in the engaged position and out of fluid communication with the fluid reservoir in the armed and storage positions. A biasing member has a proximal end and a distal end. The proximal end of the biasing member is coupled to the housing and the distal end of the biasing member is configured to deliver a force to the fluid reservoir. A piston member extends through the biasing member and is coupled to the distal end of the biasing member. The piston member is fixed with respect to the housing in a locked position such that the biasing member does not deliver the force to the fluid reservoir and is moveable with respect to the housing in a released position such that the biasing member delivers the force to the fluid reservoir. Transitioning the needle from the storage position to the armed position transitions the piston from the locked position to the released position.

In a further embodiment, the fluid delivery device comprises a hydraulic basal chamber coupled between the biasing member and the fluid reservoir. In a further embodiment, the fluid delivery device comprises a hydraulic pump chamber and a flow restrictor fluidly coupling the hydraulic pump chamber and the hydraulic basal chamber. In one embodiment, the piston includes a plunger tip coupled to the hydraulic basal chamber. In one embodiment, the piston is releaseably coupled to the housing with a pin extending through the housing and a cap extends over the needle in the storage position, the cap being coupled to the pin such that removing the cap releases the piston. In one embodiment, the biasing member comprises at least two overlapping coaxial springs.

In another embodiment, a fluid delivery device comprises a housing having a fluid reservoir. A first biasing member is coupled to the housing. A second biasing member is coupled to the first biasing member in series and at least partially overlapping the first biasing member. The first and second biasing members are configured to deliver a force to the fluid reservoir. In a further embodiment, the fluid delivery device comprises a plunger extending through the first and second biasing members. In one embodiment, the plunger is coupled to the second biasing member at a distal end and is releaseably coupled to the housing at a proximal end. In one embodiment, the plunger is releaseably coupled to the housing with a pin extending through the housing and the plunger. In one embodiment, the plunger is releaseably coupled to the housing with a pin extending through the housing and further comprising a needle cover coupled to the pin.

In a further embodiment, the fluid delivery device comprises a hydraulic basal chamber coupled between the first and second biasing members and the hydraulic pump chamber and a flow restrictor fluidly coupling the hydraulic basal chamber and the hydraulic pump chamber. In one embodiment, the hydraulic pump chamber has a cross sectional area less than the cross sectional area of the hydraulic basal chamber. In a further embodiment, the fluid delivery device comprises a sleeve coupling the first biasing member with the second biasing member. The sleeve has a length generally equal to the length of overlap between the first and second biasing members. In one embodiment, the sleeve has a body, a first flanged end and a second flanged end, the first flanged end extending radially outwardly from the body of the sleeve and configured to couple with an end of the first biasing member, and the second flanged end extending radially inwardly from the body and configured to couple with an end of the second biasing member.

In another embodiment, a fluid delivery device comprises an attachment surface configured to engage with a skin surface and having a first thermal conductance and a hydraulic pump chamber. A hydraulic basal chamber has a portion of the outer wall proximate the attachment surface and having a second thermal conductance. The second thermal conductance is greater than the first thermal conductance. A flow restrictor is fluidly coupling the hydraulic basal chamber and the hydraulic pump chamber. A fluid reservoir is coupled to the hydraulic pump chamber. The fluid reservoir is configured to contain a fluid deliverable to a patient. An actuator is coupled to the hydraulic basal chamber. The actuator is configured to pressurize the hydraulic pump chamber to transfer energy through the hydraulic basal chamber and the hydraulic pump chamber to the fluid reservoir to deliver the fluid at a sustained basal rate. In one embodiment, the attachment surface includes an insulating member.

In one embodiment, the insulating member is at least partially relieved to at least partially expose the portion of the outer wall of the hydraulic basal chamber proximate the attachment surface. In one embodiment, the fluid reservoir is at least partially spaced from the housing. In a further embodiment, the fluid delivery device comprises a housing having a bottom surface. The outer wall portion of the hydraulic basal chamber extends outwardly from the bottom surface of the housing. In one embodiment, the portion of the outer wall of the hydraulic basal chamber has an imaginary tangent generally aligned with the attachment surface. In one embodiment, the portion of the outer wall of the hydraulic basal chamber is configured to directly contact the skin surface. In one embodiment, a remainder of the outer wall of the hydraulic basal chamber has a third thermal conductance. The third thermal conductance being less than the second thermal conductance.

BRIEF DESCRIPTION OF THE SEVERAL VIEWS OF THE DRAWINGS

The foregoing summary, as well as the following detailed description of embodiments of the fluid delivery device will be better understood when read in conjunction with the appended drawings of an exemplary embodiment. It should be understood, however, that the invention is not limited to the precise arrangements and instrumentalities shown.

In the drawings:

FIG. 6B is the side cross sectional view of FIG. 6A shown in the engaged position;

FIG. 6C is the side cross sectional view of FIG. 6A shown in the engaged position after a length of time in use;

DETAILED DESCRIPTION OF THE INVENTION

Figure 1:
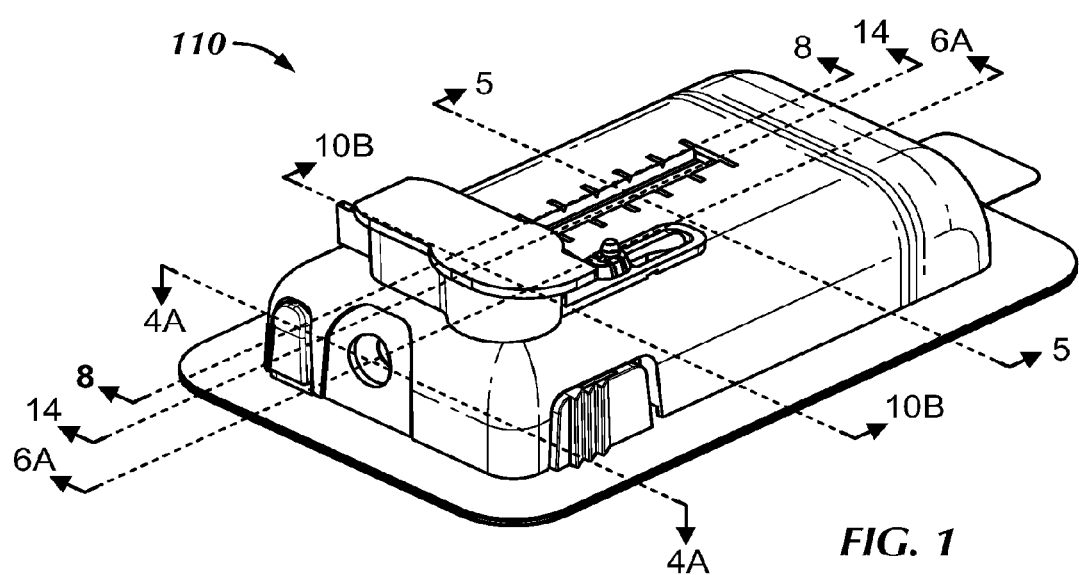
FIG. 1 is a perspective view a fluid delivery device in accordance with an exemplary embodiment of the present invention.

Referring to the drawings in detail, wherein like reference numerals indicate like elements throughout, there is shown in FIGS. 1-23C a fluid delivery device, generally designated 110, in accordance with an exemplary embodiment of the present invention. The fluid delivery device 110 may include one or more features described herein which facilitate or improve accurate delivery of a fluid and ease of use by a user or patient. The benefits provided by these features translate readily to improved patient compliance and improved therapeutic outcome.

In one embodiment, the fluid delivery device 110 is a discrete ambulatory insulin delivery pump. The fluid delivery device 110 may be single use, disposable and incapable of reuse. In preferred embodiments, the fluid delivery device 110 is completely mechanical and hydraulic and has no electronic components or aspects. The fluid delivery device 110 may provide excellent therapeutic capability in a small, single use, disposable package and can be produced using high volume manufacturing fabrication (e.g., injection molding) and assembly processes, allowing for low cost-of goods. Devices of the invention can be used for a broad range of applications, including, but not limited to, clinical applications (administration of medicaments, etc.) and biomedical research (e.g., microinjection into cells, nuclear or organelle transplantation, isolation of single cells or hybridomas, etc.).

In one embodiment, the fluid delivery device 110 is a device for dispensing, delivering, or administering the fluid or agent to the user or patient. The fluid may be any therapeutic agent. In one embodiment, the fluid is a low viscosity gel agent. In one embodiment, the fluid is an analgesic agent. In one embodiment, the fluid is insulin. In one embodiment, the fluid is a U100 insulin. In another embodiment the fluid is a U200 insulin. In another embodiment the fluid is a U300 insulin. In another embodiment, the fluid is a U500 insulin. In another embodiment the fluid is any insulin between U100 and U500. In other embodiments, the fluid may be, but is not limited to, opiates and/or other palliatives or analgesics, hormones, psychotropic therapeutic compositions, or any other drug or chemical whose continuous dosing is desirable or efficacious for use in treating patients. Single fluids and combinations of two or more fluids (admixed or co-administered) may be delivered using the fluid delivery device 110. As used herein "patients" or "user" can be human or non-human animals; the use of the fluid delivery device 110 is not confined solely to human medicine, but can be equally applied to veterinarian medicine.

The fluid delivery device 110 may dispense the fluid over a sustained period of time (i.e., basal delivery). In one embodiment, the fluid delivery rate is continuously or near continuously delivered to the user over the sustained period of time. The fluid delivery device 110 may also be capable of dispensing a supplementary amount of fluid, in addition to the basal amount, on demand, under patient control (i.e., bolus delivery). In one embodiment, as discussed further below, the bolus amount delivered in a single, selectable administration is pre-determined. In preferred embodiments, the fluid delivery device 110 is hydraulically actuated and comprises one or more reservoirs or chambers containing hydraulic fluid of a suitable viscosity for transferring power from one or more actuators to the fluid and controlling the delivery rate as discussed further below.

Figure 3:
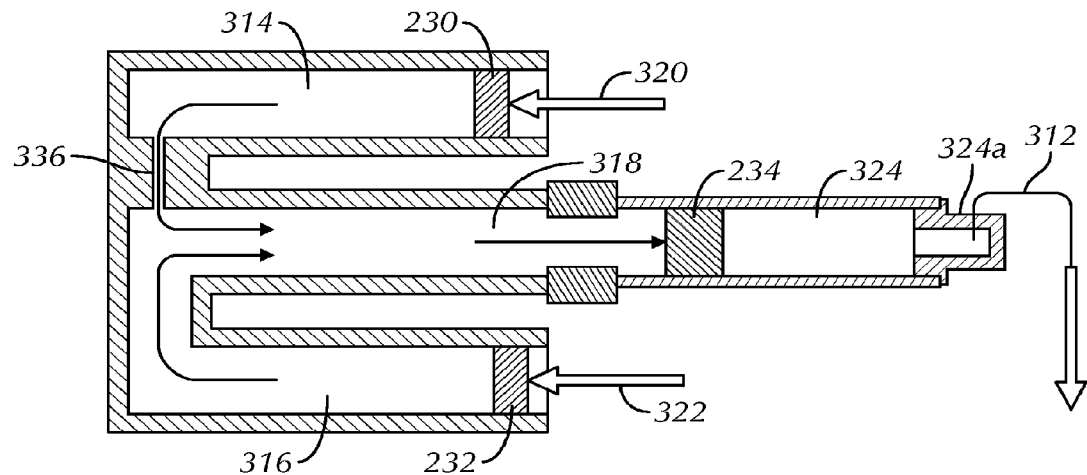
FIG. 3 is a schematic top, cross sectional view of a fluid delivery device in accordance with an exemplary embodiment of the present invention.

One exemplary embodiment of the fluid delivery device 110 is shown in the schematic of FIG. 3, illustrating select components and their relationships. The fluid delivery device 110 may have a first operable state for dispensing or delivering the fluid through an infusion set or needle 312 at a continuous or sustained basal dosage and a second operable state for delivering the fluid through the needle 312 at a bolus dosage. In some embodiments, the fluid delivery device can be in both the first and second operable states concurrently, i.e., delivering a bolus dose in addition to a basal dose of fluid. In one embodiment, the bolus dosage is a fixed incremental dosage. In another embodiment, the bolus function is capable of delivering multiple discrete bolus increments when activated by the user. In certain embodiments, the basal rate of delivery is predetermined and preset.

In one embodiment, the fluid delivery device 110 contains three hydraulic reservoirs or chambers, a hydraulic basal chamber 314, a hydraulic bolus chamber 316 and a hydraulic pump chamber 318. In some embodiments, the hydraulic bolus chamber 314 shares a common chamber with the hydraulic pump chamber 318 and/or the flow between the hydraulic bolus chamber 316 and the hydraulic pump chamber 318 is unrestricted as described further herein. In a preferred embodiment, the hydraulic basal and bolus chambers 314, 316 are separately and independently actuated by separate and independent basal and bolus actuators 320, 322.

Referring to FIG. 3, in one embodiment, the hydraulic basal and bolus chambers 314, 316 act on the hydraulic pump chamber 318 which in turn acts on a fluid reservoir or delivery chamber 324, containing the fluid. In other embodiments, the hydraulic basal and bolus chambers 314, 316 each act on a distinct pump chamber and each pump chamber is functionally connected to a separate fluid reservoir (not shown).

Figure 2:
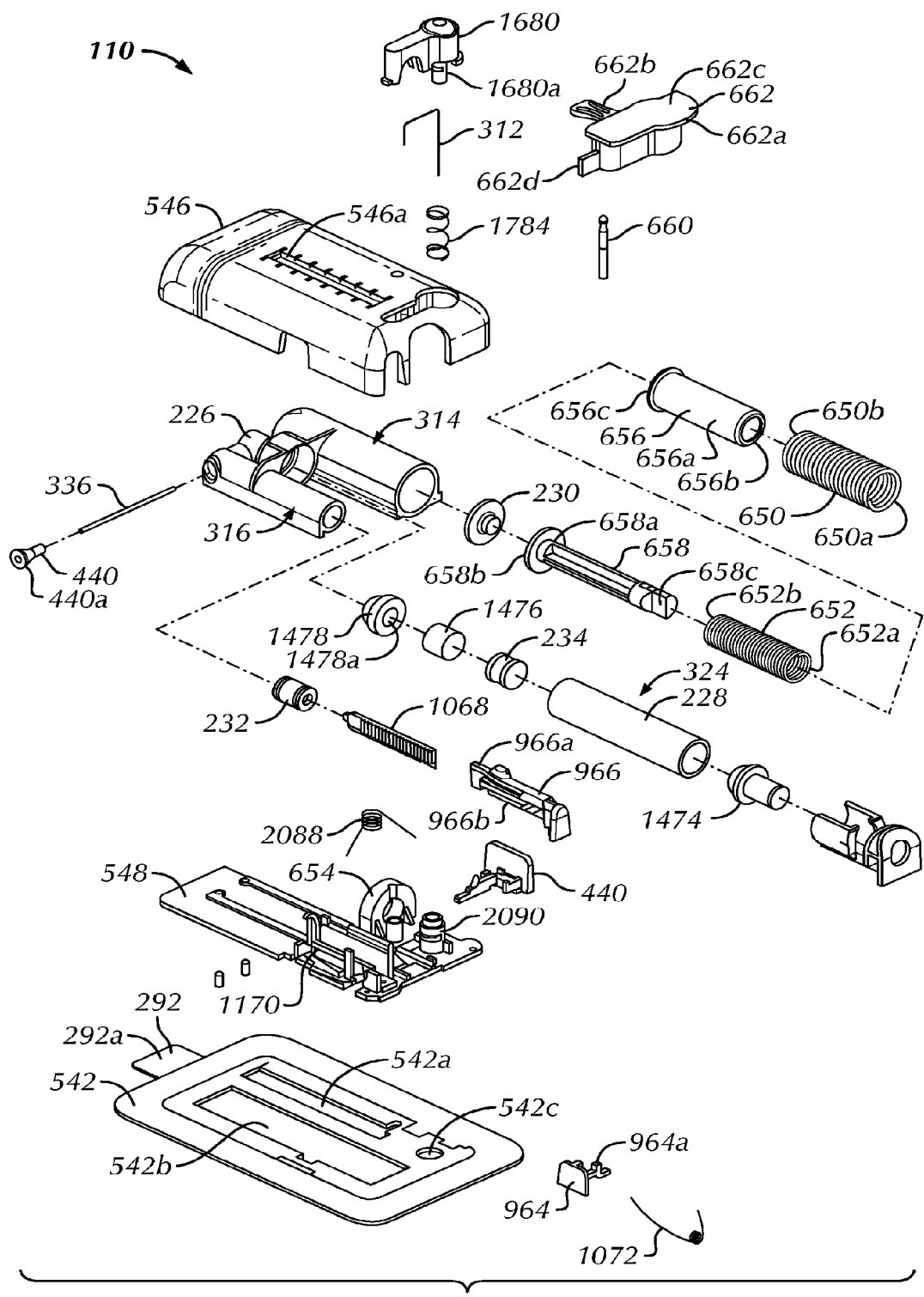
FIG. 2 is an exploded perspective view of the fluid delivery device shown in FIG. 1.

Referring to FIG. 2, the hydraulic basal, bolus and pump chambers 314, 316, 318 may be defined by a manifold 226. In one embodiment, the manifold 226 is an integral one piece component 226. In one embodiment, the manifold 226 is comprised of a polymer. In one embodiment, the manifold 226 is comprised of polyvinyl chloride (PVC). In one embodiment, the fluid reservoir 324 and a portion of the hydraulic pump chamber 318 are defined by a fluid cartridge 228. In one embodiment, the fluid cartridge 228 is comprised of a polymer. In one embodiment, the fluid cartridge 228 is comprised of Topas 6017 S-04. The hydraulic basal, bolus and pump chambers 314, 316, 318 and the fluid reservoir 324 may be cylindrical. In other embodiments, the hydraulic pump chambers 314, 316, 318 and the fluid reservoir 324 have any cross sectional shape such as square, rectangular or triangular. In one embodiment, a first moveable barrier 230 separates the basal actuator 320 and the hydraulic basal chamber 314. In one embodiment, a second moveable barrier 232 separates the bolus actuator 322 and the hydraulic bolus chamber 316. In one embodiment, a third moveable barrier 234 separates the hydraulic pump chamber 318 and the fluid reservoir 324. The first, second and third moveable barriers 230, 232, 234 may be pistons as described further below. In other embodiments, the first, second and third moveable barriers 230, 232, 234 are any barriers that can transfer movement between two chambers such as membranes or expandable walls.

The hydraulic basal and bolus chambers 314, 316 may be parallel, spaced on either side of and generally aligned with the hydraulic pump chamber 318 and the fluid reservoir 324 as illustrated in order to provide a more compact configuration. In one embodiment, the hydraulic pump chamber 318 is provided toward one side of the fluid delivery device 110. In other embodiments, the hydraulic basal, bolus and pump chambers 314, 316, 318 are arranged in any configuration that allows fluid communication and achieves the desired outer shape of the fluid delivery device 110 such as stacked in a triangle configuration.

The basal actuator 320 may act on the hydraulic basal chamber 314 containing a hydraulic fluid to pressurize the hydraulic basal chamber 314 and force a hydraulic fluid through a flow restrictor 336 into the hydraulic pump chamber 318. Generally, but not necessarily, the hydraulic fluid in hydraulic pump chamber 318 may be identical or similar in composition to the hydraulic fluid in hydraulic basal chamber 314. Actuation of the basal actuator 320 may result in a flow of hydraulic fluid from hydraulic basal reservoir 320 into the hydraulic pump chamber 318 at a reduced rate as compared to if the flow restrictor 336 was not provided. As the volume of hydraulic fluid in the hydraulic pump chamber 318 increases, the third moveable barrier 234 is displaced, compressing or reducing the volume of the fluid reservoir 324 and causing the fluid contained therein to be expelled through an output orifice or needle 312 at a sustained basal rate. In one embodiment, the basal rate is substantially constant.

In some embodiments, a bolus actuator 322 independently acts on the hydraulic bolus chamber 316. In one embodiment, the bolus actuator 322 acts directly on the hydraulic pump chamber 318. It should be understood, however, that the invention is not limited to devices comprising both a basal and a bolus capability. Devices of the invention having one or more features described herein may comprise a basal capability, a bolus capability, or both basal and bolus capabilities.

Both hydraulic bolus chamber 316 and hydraulic pump chamber 318 may contain hydraulic fluid of an appropriate viscosity. Generally, but not necessarily, the composition of the hydraulic fluid in hydraulic pump chamber 318 will be identical or similar to the composition of the hydraulic fluid in hydraulic basal and bolus chambers 314, 316. Actuation or displacement of the bolus actuator 322 independently displaces the third moveable barrier 234, compressing or reducing the volume of fluid reservoir 324 and causing the fluid contained therein to be expelled through an output orifice such as the needle 312. Concurrent operation of both the basal and bolus actuators 320, 322 causes compression of fluid reservoir 324 by an amount greater than operation of either actuator alone.

When present, both the basal and bolus actuators 320, 322 may be integrated within the hydraulically actuated system in a manner that allows each function to provide independent displacement force onto a common movable barrier 234, which in turn displaces fluid from within a common fluid reservoir 324 to dispense the fluid from the device. In other embodiments, the basal and bolus actuators 320, 322 may be integrated within the hydraulically actuated system in a manner that allows each function to provide independent displacement force onto separate moveable barriers (not shown), which in turn displace fluid from within separate fluid reservoirs (not shown). Examples of a multi-cartridge fluid delivery devices for use with the inventions presented herein are disclosed in U.S. Patent Application Publication No. 2009/0240232 which is hereby incorporated by reference in its entirety.

In one embodiment, the fluid delivery device 110 utilizes a combination of force, high, very high or ultra high viscosity fluid, and flow restriction to deliver the fluid on a continuous or sustained basis. The flow restrictor 336 may facilitate continuous delivery of fluid at a basal rate by, among other aspects, creating a large pressure differential or pressure drop between the hydraulic basal chamber 314 and the hydraulic pump chamber 318, allowing the system to tolerate a wider range of frictional variations in the system such as movement of the third movable barrier 234 within the fluid cartridge 228, tolerate small changes in the resistance to flow, and overcome potential occlusions in the flow path. In one embodiment, the pressure differential between the hydraulic basal chamber 314 and the hydraulic pump chamber 318 during use is approximately 10:1. In one embodiment, the pressure differential between the hydraulic basal chamber 314 and the hydraulic pump chamber 318 during use is approximately 46:1. In one embodiment the hydraulic basal chamber 314 operates at a pressure between approximately 20 psi and between 70 psi. In one embodiment, the hydraulic basal chamber 314 operates at a pressure of approximately 46.8 psi. In one embodiment, the hydraulic pump chamber 318 operates at a pressure of approximately 0.5 psi to approximately 5 psi. In one embodiment, the hydraulic pump chamber 318 operates at a pressure of approximately 1.2 psi.

The flow restrictor 336 is dimensionally adapted to control the rate of fluid flow there through. In one embodiment, the flow restrictor 336 has a diameter of approximately 1-1000 µm. It should be understood that all ranges provided herein encompass both the beginning and end points of the range (e.g., includes 1 and 1000 µm in a range of from about 1 to about 1000 µm), as well as all values in between. Whatever the shape of the flow restrictor 336, the cross sectional area and the length of the opening will be sized to achieve the flow rate desired. For example, the flow restrictor 336 may be about one-ten thousandths of an inch (or 2-3 µm) in diameter. Depending on use, the flow restrictor 336 size may be anything, including but not limited to a diameter between 200 nm-500 nm, or 500 nm-1000 nm, or 1-2 µm, or 5-10 µm, or 10-1000 µm. In one embodiment, the outer diameter of the flow restrictor 336 is approximately 0.026 inches and the inner diameter of the flow restrictor 336 is one of approximately 0.00758 inches, 0.00708 inches and 0.00638 inches. In one embodiment, the length and outer diameter of the flow restrictor 336 remains constant from device to device based on the size of the manifold 226 and the inner diameter of the flow restrictor 336 may be altered to achieve the desired flow rate. Other sizes and dimensions of the flow restrictor 336 can be selected, and the size and dimension selected will depend upon the application at hand and, in particular, the viscosity of the hydraulic fluid and the force applied by the basal actuator 320. In one embodiment, the flow restrictor 336 is comprised of topaz. Having a flow restrictor 336 comprised of topaz may help to ensure that the flow restrictor 336 has a substantially accurate and constant cross sectional size and shape. Those of skill in the art will understand that any suitable flow restrictor 336 may be employed, and that the size and the shape of the flow restrictor 336 can vary to achieve the desired flow rate of the fluid being mediated under the expected conditions, including temperature and ambient pressure. The flow restrictor 336 need not be circular in cross sectional shape, and can be an oval, a square, a rectangle, a triangle, a polygon, or irregular in shape. The size and shape of the flow restrictor 336 may be determined empirically by testing the fluid flow of selected fluids at conditions of interest.

Figure 4A:
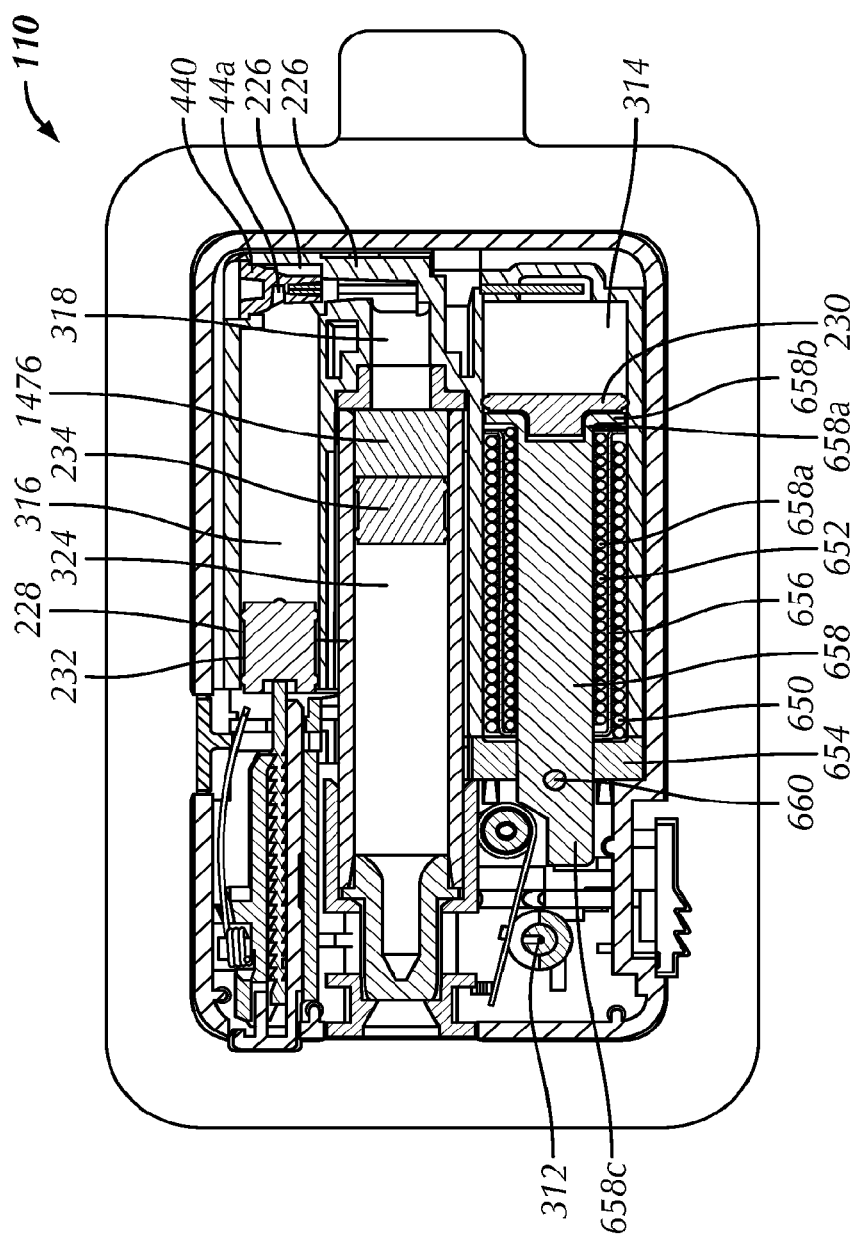
FIG. 4A is a top cross sectional view of the fluid delivery device shown in FIG. 1 taken along line 4A-4A of FIG. 1.
Figure 4B:
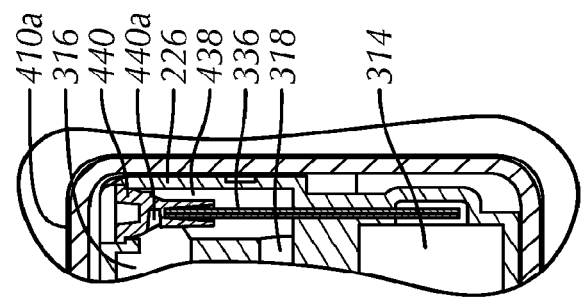
FIG. 4B is a top partial cross sectional view of the fluid delivery device shown in FIG. 1 taken along a length of a flow restrictor.

Referring to FIG. 4B, in one embodiment, the flow restrictor 336 extends through a side 410a of the fluid delivery device 110. In one embodiment, the flow restrictor 336 extends through the hydraulic bolus chamber 316 such that the hydraulic bolus chamber 316 is in fluid communication with the hydraulic basal chamber 314 through the flow restrictor 336 and the hydraulic basal and bolus chambers 314, 316 are both in fluid communication with the hydraulic pump chamber 318 through a nonrestrictive fluid passageway 438. In an alternative embodiment, the fluid passageway 438 is restrictive in order to retard the delivery rate of the bolus dose rather than having the delivery rate be nearly equal to the rate of movement of the bolus actuator 322.

With continued reference to FIG. 4B, in one embodiment, the flow restrictor 336 includes a guide plug 440. In one embodiment, the guide plug 440 is sealed with the manifold 226 and positions the flow restrictor 336 within the fluid passageway 438. In one embodiment, the guide plug 440 includes an opening 440a for fluidly coupling the flow restrictor 336 and the hydraulic bolus chamber 316. The flow restrictor 336 may be secured to the manifold 226 by an epoxy. In one embodiment, the guide plug 440 and the flow restrictor 336 are comprised of generally translucent materials such that the flow restrictor 336 may be fixed to the manifold 226 by a UV curable resin after inserting the flow restrictor 336 and the guide plug 440 within the manifold 226.

When the fluid delivery device 110 is activated, the basal actuator 320 acts on the hydraulic fluid, increasing the pressure within the hydraulic basal chamber 314. As a result of this pressure increase, the hydraulic liquid within the hydraulic basal chamber 314 begins to flow through the flow restrictor 336 into the hydraulic bolus chamber 316. In one embodiment, the bolus actuator 320 prevents expansion of the hydraulic bolus chamber 316 and the hydraulic fluid from the hydraulic basal chamber 314 flows through the fluid passageway 438 and into the hydraulic pump chamber 318 where the hydraulic fluid displaces the third moveable barrier 234 causing the fluid within the fluid reservoir 324 to exit the fluid delivery device 110 at a sustained basal rate. In one embodiment, the basal rate is predetermined or preset by the manufacturer. Embodiments of the fluid delivery device 110 may be used to continuously deliver a fluid over a range of time such as but limited to 1 min, 1 hr, 6 hrs, 12 hrs, 1 day, 3 days, 5 days, 10 days, one month, etc. In certain embodiments, the fluid is expelled from the fluid delivery device 110 at a basal rate selected from but not limited to: about 0.1 µl to about 10 µl per hour, about 10 to about 100 µl per hour, about 100 µl per hour to about 1 ml per hour, about 1 ml to about 100 ml per hour, or about 100 ml to about 200 ml per hour. In one embodiment, the basal rate is approximately 100 units/day which is 42 µl/hour or 1000 µl/24 hours. The rate and delivery period selected will depend upon the application at hand, and those of skill in the art will be able to determine the proper dosage rate for a given application.

Referring to FIG. 3, embodiments of the fluid delivery device 110 may be connected to an infusion set or needle 312 through a connection point at the distal end 324a of the fluid reservoir 324. In alternative embodiments, the needle 312 may be located on the side wall of fluid reservoir 324. The needle 312 may be substituted with any delivery device such as a lumen, a needle set, a catheter-cannula set or a microneedle or microneedle array attached by means of one or more lumens.

In one embodiment, basal flow rate is preset at the time of manufacture based on the selection of the flow restrictor 336 in combination with the viscosity of the hydraulic fluid and the force supplied on the hydraulic basal chamber 314. Alternatively, the length and/or diameter of the flow restrictor 336 can be adjusted on demand to alter the basal flow rate. In other embodiments, the flow restrictor 336 may be adjustable in size, as by means of an adjustable iris-type aperture or telescoping restrictor passage miniature valve or paired gating slits (not shown). In an alternate embodiment, an electrical motor or piezoelectric device (not shown) may be used to open or close the aperture, thus affecting the rate at which hydraulic fluid flows into pump chamber and displaces the third moveable barrier 234.

The hydraulic fluid may be any non-compressible, flowable material such as gel or a collection of miniature solid beads. In one embodiment, the hydraulic fluid is an ultra pure, bio-inert material. In one embodiment the hydraulic fluid is silicon oil. Useful viscosity of the hydraulic fluid is limited at its upper bound by the size of the flow restrictor 336. At its lower bound, the hydraulic fluid must be viscous enough that the flow of the hydraulic fluid can remain highly regulated by the combination of the pressure from the basal actuator 320 and the size of the flow restrictor 336 under a wide range of environmental conditions, especially in the presence of low atmospheric pressure and/or high ambient temperature (where viscosity tends to decrease).

As used herein, "high viscosity" means the working hydraulic fluid has a viscosity grade of at least about ISO VG 20, or at least about ISO VG 32, or at least about ISO VG 50, or at least about ISO VG 150, or at least about ISO VG 450, or at least about ISO VG 1000, or at least about ISO VG 1500 or more. In one embodiment the hydraulic fluid is very high viscosity fluid. As used herein, "very high viscosity" means the working hydraulic fluid has a viscosity of from about 80,000 to about 180,000 cPs. In one embodiment the hydraulic fluid is ultra high viscosity fluid (e.g., from about 180,000 to about 200 cPs). In one embodiment, the hydraulic fluid has a viscosity of 100,000 centiStokes.

In one embodiment, since viscosity varies inversely with temperature it is important to keep the hydraulic fluid at a generally constant temperature. The fluid delivery device 110 is worn on the user's body for the duration of administration of the fluid. The fluid delivery device 110 may be dimensionally adapted to attach to a user's body via an adhesive patch 542 (see FIG. 5) as described further below. Accordingly, the fluid delivery device 110 will be exposed to a range of environmental conditions commensurate with the patient's lifestyle. Without appropriate control of the variation in temperature of the hydraulic fluid, higher environmental temperatures may cause a reduction in viscosity, resulting in an increase in fluid flow and lower environmental temperatures may cause an increase in viscosity, resulting in a decrease in fluid flow. In one embodiment, the hydraulic fluid is brought to a generally constant temperature corresponding to the temperature of the user's skin. Thus, in some embodiments, the configuration of the fluid delivery device 110 reduces the effect of environmental temperature on the temperature of hydraulic fluid in the device. In one embodiment, because the temperature of the user's skin is likely higher than the storage temperature of the hydraulic fluid, the initial fluid delivery rate is ramped up to the sustained basal delivery rate.

Figure 5:
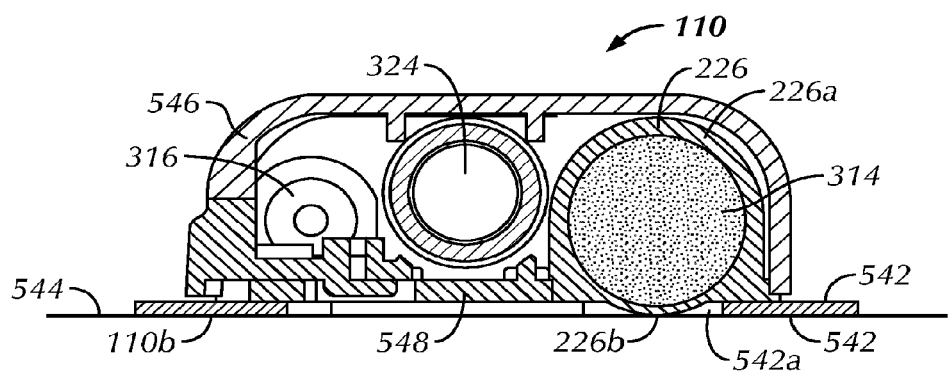
FIG. 5 is a front cross sectional view of the fluid delivery device shown in FIG. 1 taken along line 5-5 of FIG. 1.

Referring to FIG. 5, the fluid delivery device 110 may comprise a conductive thermal couple between the hydraulic fluid in the fluid delivery device and the body of the wearer. The thermal couple utilizes the consistent temperature of the body to regulate or moderate the temperature of the hydraulic fluid which might otherwise be subject to wide variation as a result of environmental temperature changes. This modulation reduces variation in the viscosity of the hydraulic fluid, thereby reducing undesired variation in the flow or delivery of the fluid caused by changes in ambient temperature.

In one embodiment, a thermally conductive path is provided between a hydraulic basal chamber 314 and the skin. The fluid delivery device may have an attachment surface 542a having a first thermal conductance configured to engage with a skin surface 544. In one embodiment, the manifold 226 housing the hydraulic basal chamber 314 has an outer wall 226a. In one embodiment, the outer wall 226a has a portion 226b proximate the attachment surface 542a having a second thermal conductance; the second thermal conductance being greater than the first thermal conductance of the attachment surface 542a. The portion 226b of the manifold proximate the attachment surface 542a may be in direct contact with the skin surface 544 to allow for the hydraulic fluid within the hydraulic basal chamber to be kept at a substantially constant temperature corresponding to the temperature of the skin surface 544. In one embodiment, the attachment surface 542a is integral with an outer housing 546. In one embodiment, the attachment surface 542a is integral with a base 548 that is attached to the housing 546 (see FIG. 2). As used herein, the base 548 may be considered to be part of the housing 546.

In another embodiment, thermal insulation is provided around the remaining surfaces of the hydraulic basal chamber 314 that are exposed, directly or indirectly such as through the housing 546 to the outside environment. The thermal insulation may be any thermally conductive material and or an air space as shown. In a preferred embodiment, a thermally conductive path is coupled with thermal insulation against the outside environment (FIG. 5). In order to optimize the conductive coupling between the skin surface 544 body and the hydraulic fluid, the hydraulic basal chamber 314 may be positioned in direct contact with the body of the wearer. The fluid delivery device 110 may also be worn on the belly of the user and covered with clothing to help further reduce the impact of changes in the ambient temperature.

As shown in FIG. 5, the portion 226b of the manifold 226 housing the hydraulic basal chamber 314 may be proud of the surrounding surface of the base 548. In one embodiment, the portion 226b of the manifold 226 extending from the base 548 is generally tangent with attachment surface 542a of the adhesive patch 542 such the entire bottom surface 110b of the fluid delivery device 110 is substantially planar. If present, the adhesive patch or pad 542 that affixes the fluid delivery device 110 to the skin surface 544 is preferably relieved in this area, relief area 542a to further assure contact between the outer reservoir wall and the skin (see also FIG. 2). The adhesive patch 542 may partially extend below or over the manifold 226 to prevent the side of the manifold from extending through relief area 542a upon movement of adhesive patch extending outwardly from the fluid delivery device 110. In one embodiment, the outer wall of the manifold 226 may be thinned (as shown) or the housing or other materials may be relieved in the area which contacts the skin surface 544 proximate the hydraulic basal chamber 314 in order to reduce the mass of material separating the hydraulic fluid and the user to increase the thermal couple between the body and the hydraulic fluid.

In order to further reduce the influence of the outside environmental temperature on the temperature of the hydraulic fluid, one or more additional features may be incorporated into the device to insulate and isolate the hydraulic fluid from the outside environment. The hydraulic basal chamber 314 can be a separate or isolated component from the remainder of the manifold (not shown). In one embodiment, the manifold 226 and the housing 546 may be separated by an open air gap in the areas that face toward the outside environment. To further isolate the hydraulic liquid, the air gap between the hydraulic basal chamber and the housing 546 can be divided into separate air pockets to further decouple or insulate the air within this gap. In one embodiment, the fluid reservoir 324 is thermally isolated from the skin surface 544. In one embodiment, the air gap within the housing 546 substantially surrounds the fluid reservoir 324 to keep the fluid at a cooler temperature than the skin surface 544.

In one embodiment, one or more of the above configurations permits the fluid delivery device 110 to operate within a temperature range of 40° F. (5° C.) to 104° F. (40° C.). In the absence of a thermal coupling and if the hydraulic liquid were exposed to this full temperature range during operation, the amount of resulting flow variation as a result of the change in the viscosity of the hydraulic liquid (typically on the order of a 1% shift in viscosity per a 1° F. shift in temperature) could introduce too large a variation in the flow of the hydraulic fluid through the flow restrictor 336 yielding unacceptable drug delivery performance. In one embodiment, the improved temperature regulation features of the fluid delivery device 110 result in less than a 1% shift in viscosity per a 1° F. shift in ambient temperature. For example, the features may result in a change of about 0.15%, 0.10% or 0.05% shift in viscosity per 1° F. shift in temperature. In one embodiment, only an approximate 6° F. difference exists between the skin surface 544 and the hydraulic liquid at the low temperature limit and little to no difference exists between the two measurements at the high temperature limit. As a result of this efficient couple between the skin surface 544 and the hydraulic liquid, a change in temperature of less than 10° F. may be observed in the hydraulic liquid over a 65° F. change in ambient (environmental) temperature.

Figure 6A:
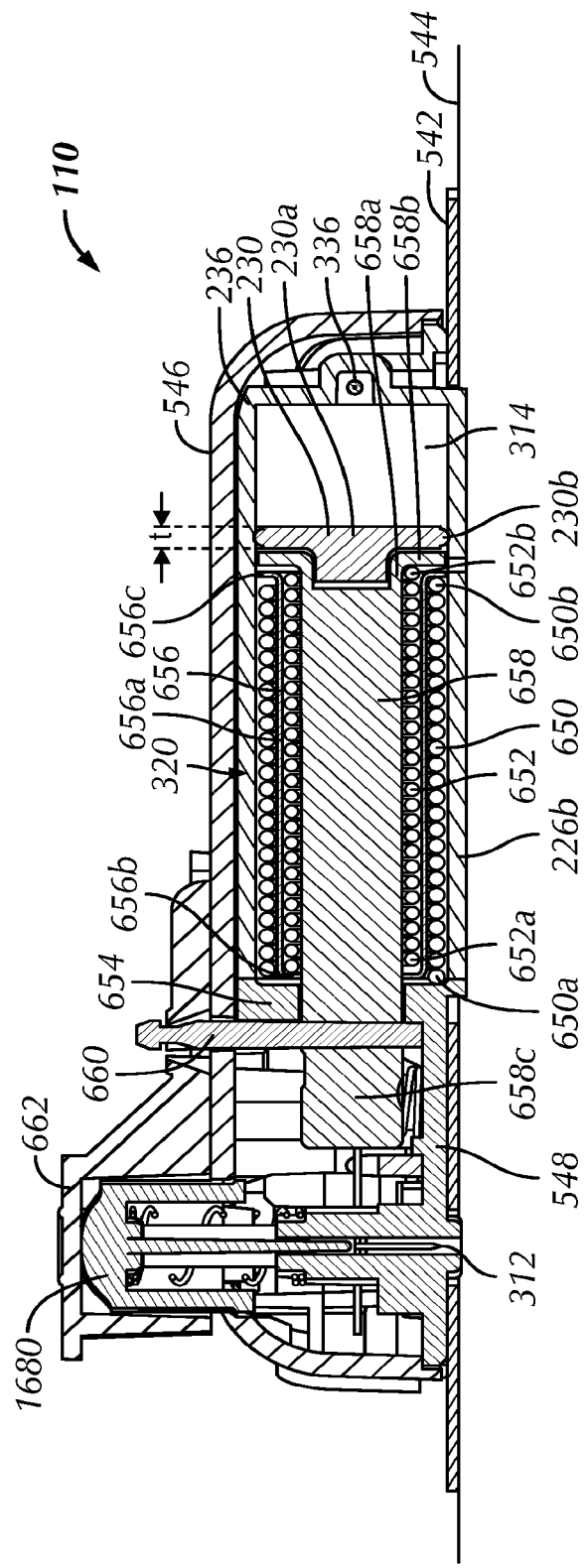
FIG. 6A is a side cross sectional view of a basal hydraulic chamber and biasing members of the fluid delivery device shown in FIG. 1 taken along line 6A-6A of FIG. 1 show in an initial position.

Referring to FIGS. 6A-6C, in one embodiment, the basal actuator 320 exerts a force on the hydraulic basal chamber 314 to pressurize the hydraulic fluid. The basal actuator 320 may be any device that applies a force on the hydraulic basal chamber 314 such as, but not limited to a peristaltic actuator, miniaturized bellows crank, or paired rollers bearing on hydraulic basal chamber 314, ratchet or stepper motor driven units that compress plates or other structures bearing on the hydraulic basal chamber 314, electrically driven or piezoelectric mechanisms, expanding gas volume, thermal energy, or any other device or process capable apply a pressure, either directly or indirectly, to the fluid being delivered. In one embodiment, the basal actuator 320 is open loop such that no electronics are required and the fluid delivery device 110 may be purely mechanical.

In one embodiment, the basal actuator 320 is comprised of one or more biasing members such as a first biasing member 650 and a second biasing member 652. In one embodiment, the one first and second biasing members 650, 652 are springs. In one embodiment, the first and second biasing members 650, 652 are helical compression springs. The force exerted by a spring in a compressed state at the start of travel is greater than the force exerted by the spring in a less compressed state toward the end of travel. The resulting force differential can impact the flow of hydraulic fluid within the fluid delivery device 110 and thus impact the flow of the fluid being delivered.

In one embodiment, the difference in the force exerted by the first and second biasing members 650, 652 between the initial compressed state and the less compressed state is reduced, thus reducing the amount of possible variation in the device's ability to achieve a sustained fluid delivery rate. In one embodiment, the force differential between the compressed and less compressed state is minimized by reducing the spring rate (force/deflection) of the spring. The spring rate may be reduced by increasing the length of the spring. In one embodiment, in order to keep the fluid deliver device 110 as compact in size as possible and prevent the basal actuator 320 from having a decreased forced from beginning to end, multiple, coaxial stacked biasing members are used. In an alternative embodiment, the second biasing member 652 is coupled to the first biasing member 650 in parallel. However, overlapping the first and second biasing members 650, 652 further reduces the size of the fluid delivery device 110. In one embodiment, the cross sectional area of the hydraulic basal chamber 314 is larger than the cross sectional area of the fluid reservoir 324 to move the third moveable barrier 234 a greater axial distance than the axial distance traveled by the first moveable barrier 230 (see e.g. FIG. 4A). Reducing the spring force attenuation that occurs over the total travel of the spring (stroke) during operation and maintaining a more constant spring force on the hydraulic fluid produces a more consistent flow of fluid from the device.

Referring to FIG. 6A, in one embodiment, the second biasing member 652 is coupled to the first biasing member 650 in series and at least partially overlaps the first biasing member 650. In one embodiment, the first biasing member 650 is co-axial with the second biasing member 652. A co-axial arrangement of the first biasing member 650 and the second biasing member 652 may be preferred over a parallel arrangement. In one embodiment, a proximal end 650a of the first biasing member 650 is coupled to the housing 546. In one embodiment, the proximal end 650a abuts against a stop 654 extending from the base 548 (see also FIG. 2). In one embodiment, a sleeve 656 couples a distal end 650b of the first biasing member with a proximal end 652a of the second biasing member 652, the sleeve 656 having a length generally equal to the length of overlap between the first and second biasing members 650, 652. In one embodiment, the sleeve 656 has a body 656a, a first flanged end 656c and a second flanged end 656b. The first flanged end 656c may extend radially outwardly from the body 656a of the sleeve 656 to engage the distal end 650b of the first biasing member 650. The second flanged end 656b of the sleeve 656 may extend radially inwardly from the body 656a of the sleeve 656 to engage a proximal end 652a of the second biasing member 652. The body 656a of the sleeve 656 may be generally hollow to allow the second biasing member 652 to extend through the sleeve 656 and engage the second flanged end 656b. In one embodiment, the first and second biasing members 650, 652 have substantially equal spring rates such that the sleeve 656 "floats" between the first and second biasing members 650, 652 as they both expand. If one biasing member were stronger than the other, the stronger biasing member may dominate, preventing the other biasing member from expanding and negating the benefit of the multi-biasing member configuration. In one embodiment, the difference in spring rate between the first and second biasing members 650, 652 is no greater than approximately 10%. In one embodiment, the difference in spring rate between the first and second biasing members 650, 652 is no greater than approximately 3%.

The basal actuator 320 may include a plunger 658 extending through the first and second biasing members 650, 652. In one embodiment, the distal end 658a of the plunger 658 has a radially outwardly extending flange 658b. The flange 658b of the plunger 658 may engage the first moveable barrier 230 and the distal end 652b of the second biasing member 652. A proximal end 658c of the plunger 658 may be releaseably coupled with the stop 654. The plunger 658 may extend through the stop 654 and be releaseably coupled to the housing with a pin 660. In one embodiment, the pin 660 extends through the housing 546 and at least partially through the plunger 658 and abuts against the stop 654 such that the pin 660 prevents the plunger 658 from extending further into the hydraulic basal chamber 314 due to the force of the first and second biasing members 650, 652 and can be removed from outside of the housing 546. In one embodiment, the pin 660 is tapered to facilitate easier removal of the pin 660. The pin 660 may be coupled with a button cover 662 such that removal of the button cover 662 releases the plunger 658 in one step by the user as described further below. FIGS. 6A-6C illustrate the basal actuator 320 in the initial position (FIG. 6A), immediately after removing the pin 660 to activate or initiate the basal actuator 320 (FIG. 6B) and the basal actuator 320 in use after a period of delivering the fluid (FIG. 6C).

Figure 7:
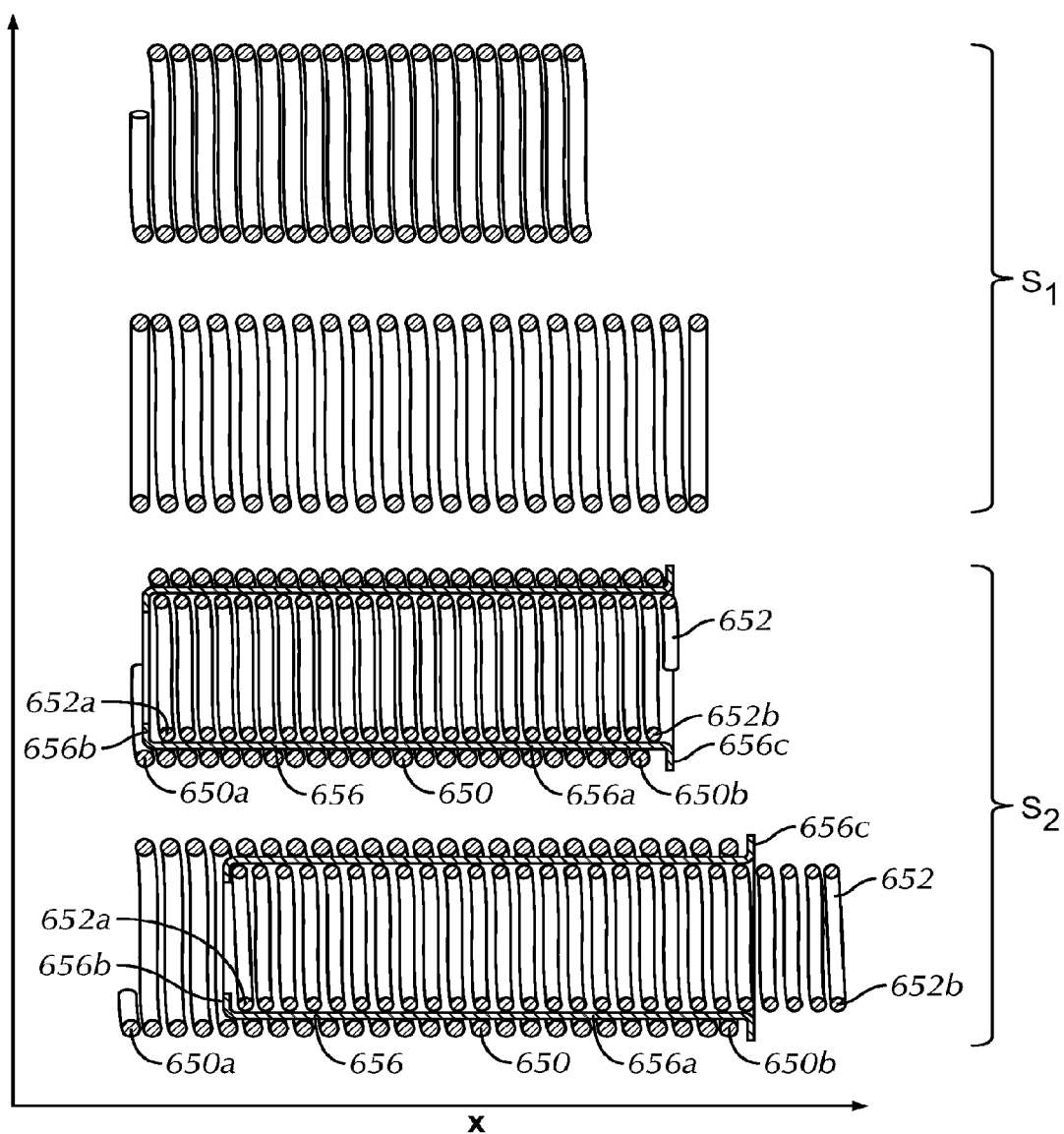
FIG. 7 includes side cross sectional views of first and second biasing members of the fluid delivery Device shown in FIG. 1 in comparison with side cross sectional views of a conventional single biasing member.

Referring to FIG. 7, in one embodiment the configuration of the first and second biasing members 650, 652 reduces the drop in force applied to the hydraulic basal chamber 314 due to the expansion of the first and second biasing members 650, 652. For example, a single compression spring $S_1$ compressed to a height of 0.75 inches will apply a force of 5.7 pounds. When this single spring $S_1$ extends to a height of 0.935 inches, the force applied drops to 5.34 pounds. This 6.3% drop in force would result in a proportional drop in hydraulic flow rate and in turn basal delivery rate of fluid from the fluid delivery device 110. To increase the volume of the fluid displaced by the fluid delivery device 110 without increasing the drop in force, the basal actuator 320 would need to be lengthened proportional to the volume increase required. In one exemplary embodiment, a dual overlapped spring configuration $S_2$ compressed to a height of 0.945 inches will apply a force of 5.7 pounds. When the dual springs $S_2$ extend to a height of 1.283 inches, the force drops to 5.34 pounds. This 6.3% drop in force would be proportional to the drop in flow rate; however, unlike the single spring $S_1$ the displacement volume is 83% greater while the length of the spring assembly is only 25% greater. The dual spring assembly $S_2$ provides an additional 83% increase in spring extension for a given loss of 0.36 pounds in spring force. This provides additional basal capacity without increasing losses due to spring extension. Conversely, the dual spring $S_2$ could be used to deliver an equivalent volume (as compared with a single spring embodiment $S_1$), with far less losses due to spring extension over an equivalent extension length (approximately a 45% decrease in the force drop over an equivalent extension length). It is understood that a dual spring arrangement as shown is but one embodiment, and that three or more springs may also be utilized.

In one embodiment, the basal actuator 320 has less than a 10% drop in force applied to the hydraulic basal chamber 314 from beginning of delivery to end of delivery. In one embodiment, the basal actuator 320 has less than an 8% drop in force applied to the hydraulic basal chamber 314 from beginning of delivery to end of delivery. In one embodiment, the basal actuator 320 has less than a 6% drop in force applied to the hydraulic basal chamber 314 from beginning of delivery to end of delivery. In one embodiment, the basal actuator 320 has less than a 5% drop in force applied to the hydraulic basal chamber 314 from beginning of delivery to end of delivery. In one embodiment, the basal actuator 320 has less than a 4% drop in force applied to the hydraulic basal chamber 314 from beginning of delivery to end of delivery. In one embodiment, the basal actuator 320 has less than a 3% drop in force applied to the hydraulic basal chamber 314 from beginning of delivery to end of delivery.

In one embodiment, the basal actuator 320 has less than a predetermined drop in force applied to the hydraulic basal chamber 314 from beginning of delivery to end of delivery as described above and has a length less than approximately 2 inches. In one embodiment, the basal actuator 320 has less than a predetermined drop in force applied to the hydraulic basal chamber 314 from beginning of delivery to end of delivery as described above and has a length less than approximately 1.5 inches. In one embodiment, the basal actuator 320 has less than a predetermined drop in force applied to the hydraulic basal chamber 314 from beginning of delivery to end of delivery as described above and has a length less than approximately 1 inch. In one embodiment, the basal actuator 320 has less than a predetermined drop in force applied to the hydraulic basal chamber 314 from beginning of delivery to end of delivery as described above and has a length less than approximately 0.8 inches.

Referring to FIG. 4A, in one embodiment, delivery consistency of the fluid is improved by reducing the amount of variation in force required to displace the third moveable barrier 234. In preferred embodiments, the force required to displace the third moveable barrier 234 is reduced or controlled by limiting or controlling one or more of the contact area, contact force and coefficient of friction between the moveable barriers 230, 232, 234 and their chamber walls and the compressibility of the hydraulic fluid and the first moveable barrier 230.

Referring to FIG. 6A, the first moveable barrier 230 may have a thickness t that is the minimum thickness to create a seal. In one embodiment, the first moveable barrier has a thickness t of approximately 0.05 inches. In one embodiment, the first moveable barrier 230 has a projection 230a that extends into the distal end 658a of the plunger 658. In one embodiment, the first moveable barrier 230 includes a rounded outer periphery 230b for contacting the inside surface of the manifold 226. In one embodiment, the outer periphery 230b of the first moveable barrier 230 is integral with the remainder of the first moveable barrier 230. In one embodiment, the first moveable barrier 230 is comprised of Bromo-Butyl Rubber. In one embodiment, the first moveable barrier 230 has a durometer of 40 shore A.

Figure 8:
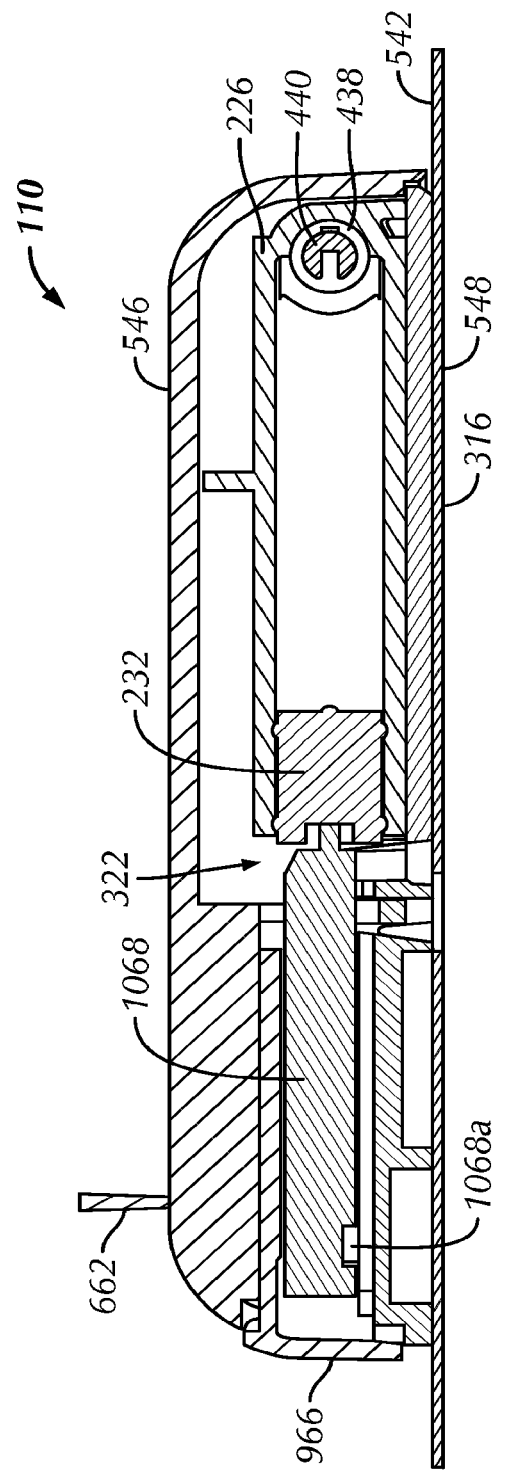
FIG. 8 is a side cross sectional view of a bolus button and a bolus hydraulic chamber of the fluid delivery device shown in FIG. 1 taken along line 8-8 in FIG. 1.
Figure 9A:
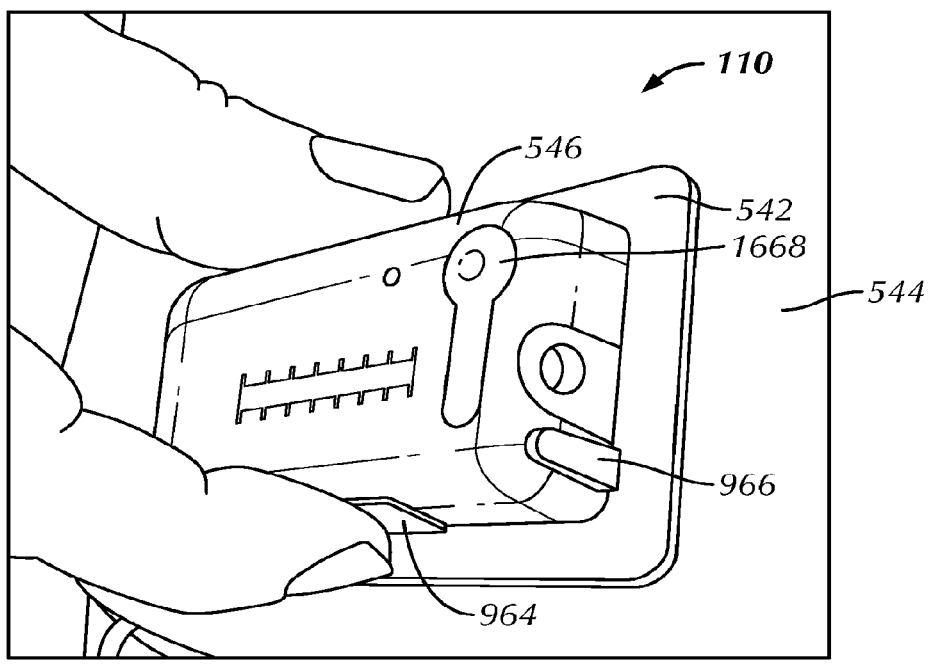
FIG. 9A is an illustrative perspective view of the fluid delivery device shown in FIG. 1 in the engaged position on a user and showing the user unlocking a bolus button.
Figure 9B:
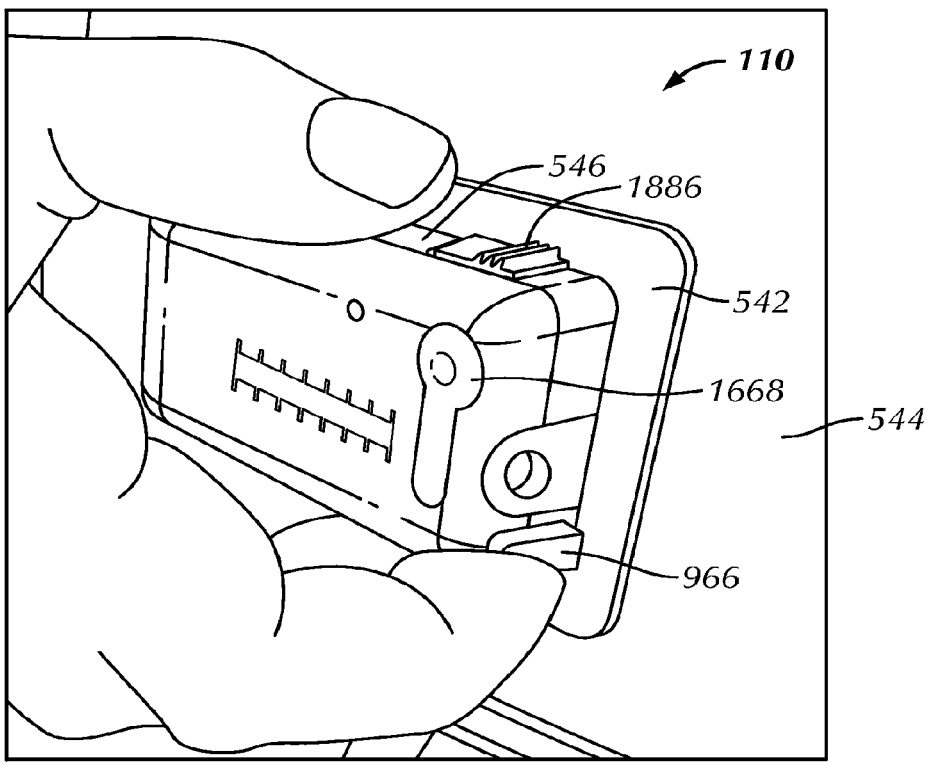
FIG. 9B is an illustrative perspective view of the fluid delivery device shown in FIG. 1 in the engaged position on the user and showing the user pressing the bolus button.

Referring to FIGS. 8-9B, in one embodiment, the fluid delivery device 110 is capable of dispensing fluid continuously or near continuously at a basal rate, as well as dispensing a supplementary amount of fluid or bolus on demand or under patient control. The fluid delivery device 110 may allow for the user to deliver multiple discrete bolus amounts without the user having to look at the fluid delivery device 110 or set the bolus amount for delivery under and through the user's shirt (not shown). Each bolus dose may require two distinct motions to deliver the bolus dose. In one embodiment, a multiple button sequence to be performed by the user to improve deliberate and correct bolus dosing. In a preferred embodiment, the bolus delivery is operated by a cyclic (i.e., common, consistent, routine) mechanical system in which the user executes the same action one or multiple times to achieve one or multiple bolus doses per cycle.

The number of bolus increments as well as the volume or dose per bolus increment may be preset at the time of manufacture based on the selection of component parameters as described further below. The fluid delivery device 110 can be preconfigured in a number of ways (fast/slow basal rate, large/small bolus volume, many/few bolus increments) to facilitate a variety of therapeutic needs.

Referring to FIGS. 9A and 9B, in one embodiment, each bolus delivery is individually and deliberately activated by the user. For example, in one embodiment each bolus delivery requires multiple (two or more) independent actions by the user, such as button actuations (via a bolus release button 964 and a bolus button 966), to insure that each bolus increment (dose) is delivered by deliberate and intentional means and not accidentally, incorrectly, or inadvertently delivered. The bolus button 966 and bolus release button 964 may be located on different sides of the fluid delivery device 110. The user may slide his or her finger along a first side of the fluid delivery device 110 until the bolus release button 964 is depressed and continue sliding their finger up a second side of the fluid delivery device 110 until the bolus button 966 is depressed. The user may slide their finger along the sides of the fluid delivery device 110 in order to find the bolus and bolus release buttons 964, 966 and the direction of movement of the user's finger or orientation of side of the fluid delivery device 110 and/or the configuration of the bolus and bolus release buttons 964, 966 help to indicate to the user which button is being depressed without having to look at the fluid delivery device 110. In one embodiment, the bolus button 966 and the bolus release button 964 are on two different sides of the fluid delivery device 110. In one embodiment, the different sides of the fluid delivery device 110 have different length to facilitate tactile feedback when administering a bolus dose, allowing operation without direct line of sight (e.g., operating the fluid delivery device 110 under one or more articles of clothing). In one embodiment, the bolus button 966 and the bolus release button 964 are located on the same side of the fluid delivery device 110. In addition, an audible "click" feedback provided by depression of either button 964, 966 may further facilitate predictable operation. In one embodiment, the bolus and bolus release buttons 964, 966 each have a distinct sound.

As illustrated in FIGS. 9A and 9B, the bolus release button 964 is depressed (FIG. 9A) prior to depressing the bolus button 966 (FIG. 9B). In one embodiment, the bolus release button 964 enables the bolus actuator 322 for actuation by the bolus button 966 such that the bolus button 966 cannot be activated absent enablement by the bolus release button 964. When the user is ready to deliver a bolus dose of fluid, he or she depresses the bolus release button 964. When depressed, the bolus release button 964 enables the bolus button 966 and after depressing the bolus button 966 causes the bolus actuator 322 to advance one bolus increment.

In some embodiments, the fluid delivery device 110 delivers a discrete dosage unit per actuation; the appropriate dosage unit will vary depending on the fluid to be delivered. In particular embodiments, for example for delivery of insulin, the fluid delivery device 110 delivers from 1 to 4 units of insulin (e.g., 0.01 to 0.04 mL) per bolus increment (per "click"). In certain embodiments, the fluid delivery device 110 is capable of delivering 36 bolus units (e.g., of insulin) in 2 unit increments, i.e., 36 units delivered over the course of 18 "clicks." At the same time, the fluid delivery device 110 may delivering an additional amount (e.g., 20, 30, 40, etc. units) at the basal rate over the entire delivery period. The total fluid capacity of the fluid delivery device 110 is the sum of the basal and bolus capacities. In some embodiments, the fluid delivery device 110 has a total fluid capacity of 56, 66 or 76 units. In other embodiments, the fluid delivery device has a total fluid capacity of about 1200, 1500, or 2000 units.

Figure 10A:
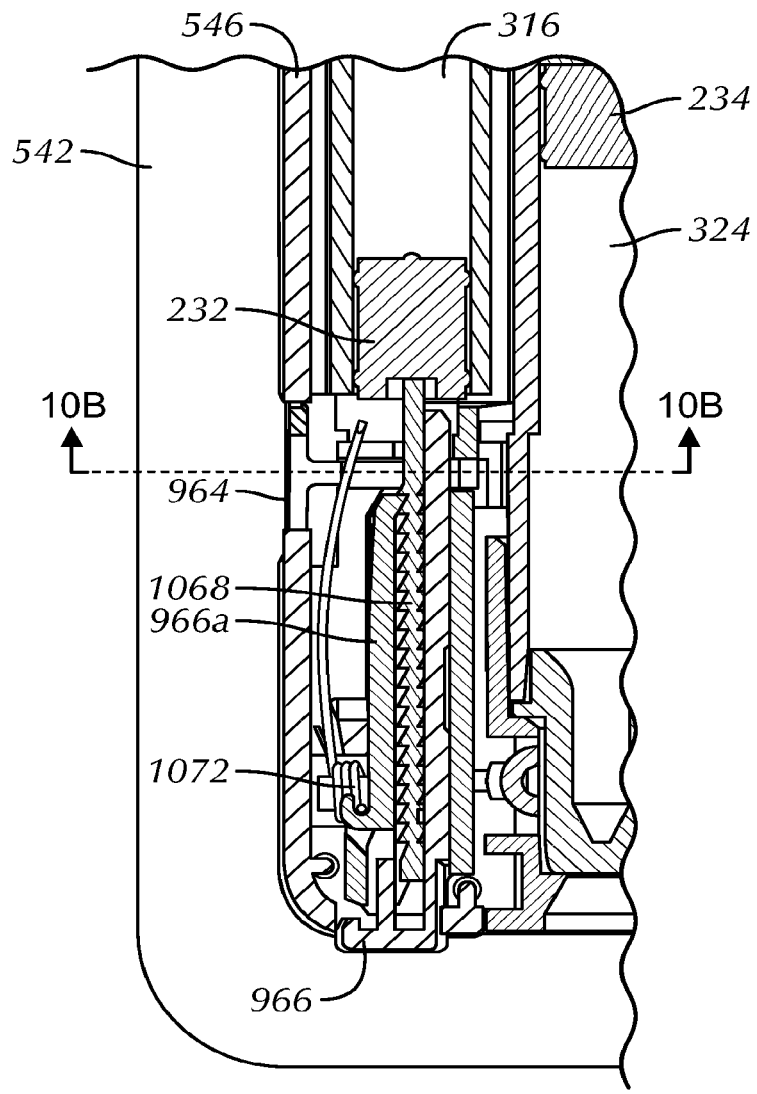
FIG. 10A is a partial, top, cross sectional view of the fluid delivery device shown in FIG. 1 taken along line 4A-4A with the bolus button in an initial locked position.

Referring to FIG. 10A, the bolus actuator 322 may include a position lock or rack 1068 that couples the bolus button 966 and the second moveable barrier 232. In one embodiment, the rack 1068 engages a housing pawl 1170 (see FIGS. 11A and 2) fixed relative to the manifold 226 that prevents the rack 1068 and second moveable barrier 232 from moving outwardly toward the bolus button 966. In one embodiment, the bolus button 966 is spring biased away from the second moveable barrier 232 and includes a pawl 966a that engages with the rack 1068 to advance the rack 1068 one or more predetermined one way ratchets or teeth and resets once permitted.

Figure 10B:
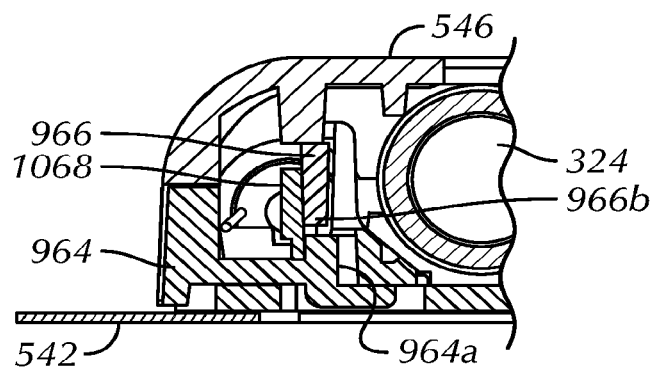
FIG. 10B is a partial, front, cross sectional view of the fluid delivery device shown in FIG. 10A taken along line 10B-10B.
Figure 11A:
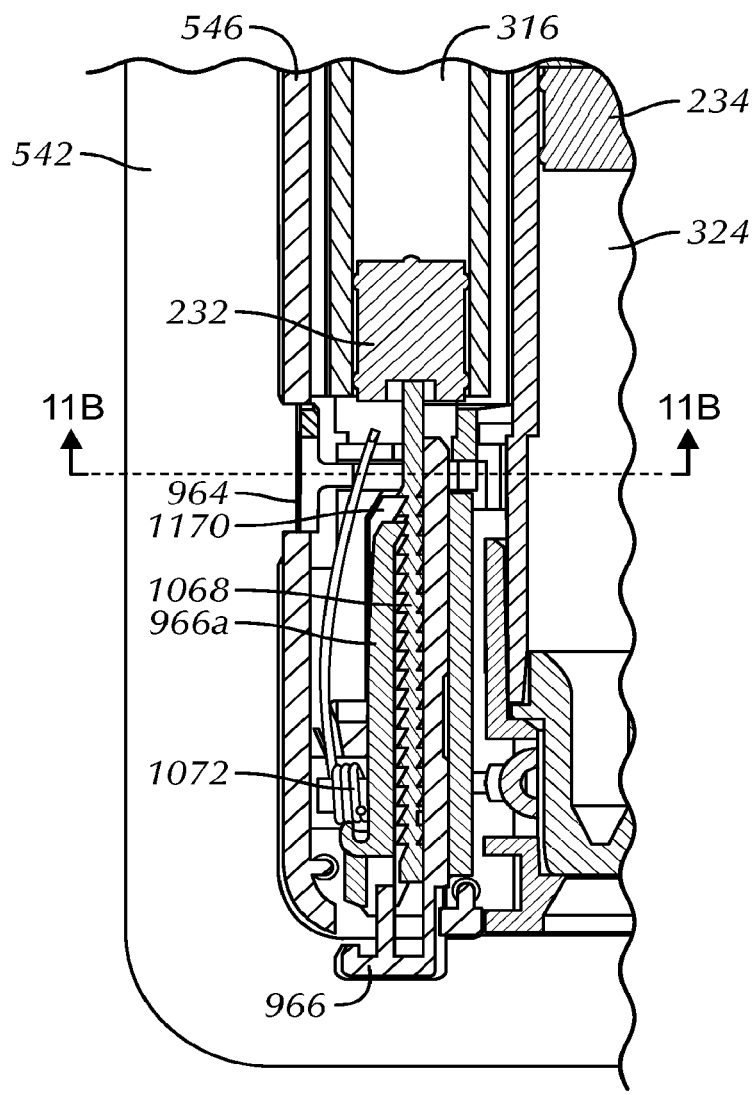
FIG. 11A is a partial, top, cross sectional view of the fluid delivery device shown in FIG. 1 taken along line 4A-4A with the bolus button in the released position.
Figure 11B:
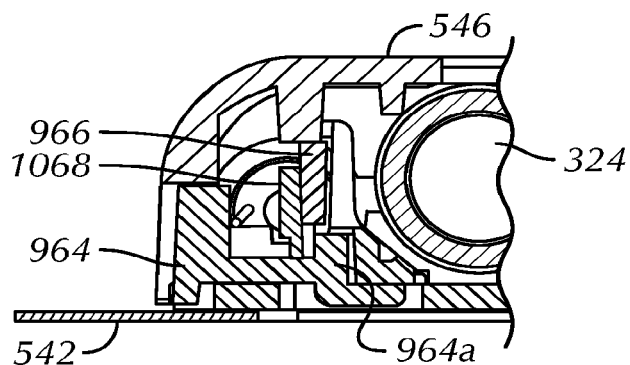
FIG. 11B is a partial, front, cross sectional view of the fluid delivery device shown in FIG. 11A taken along line 11B-11B.
Figure 12A:
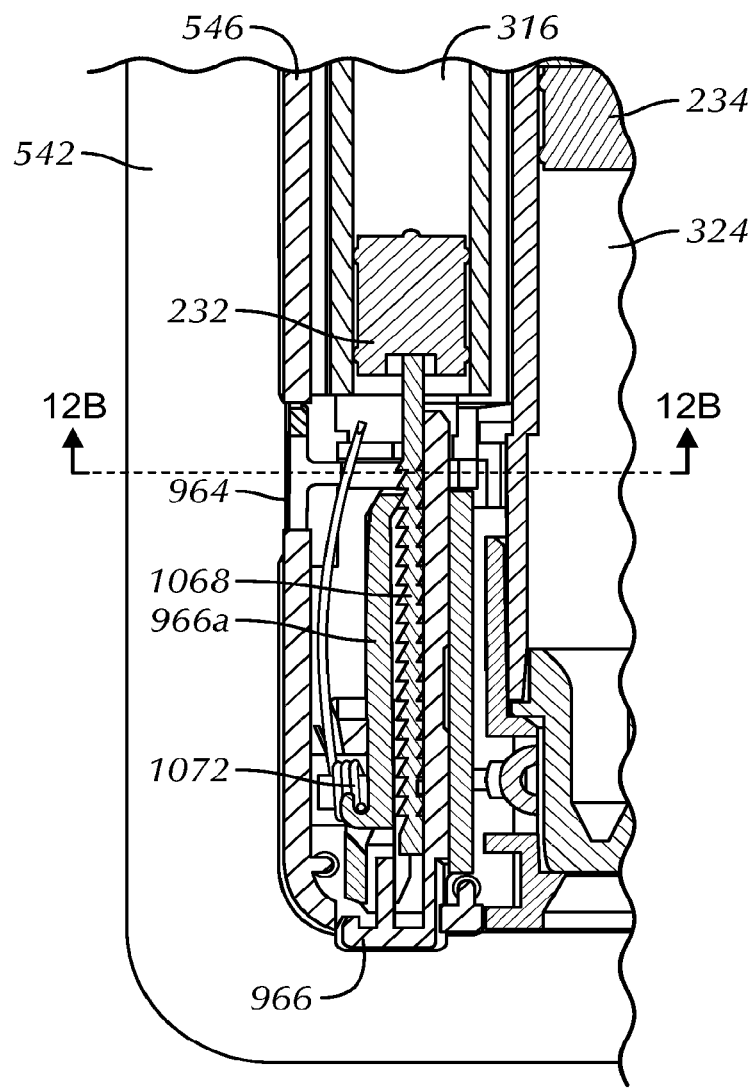
FIG. 12A is a partial, top, cross sectional view of the fluid delivery device shown in FIG. 1 taken along line 4A-4A with the bolus button in a locked position after delivery a bolus dose.
Figure 12B:
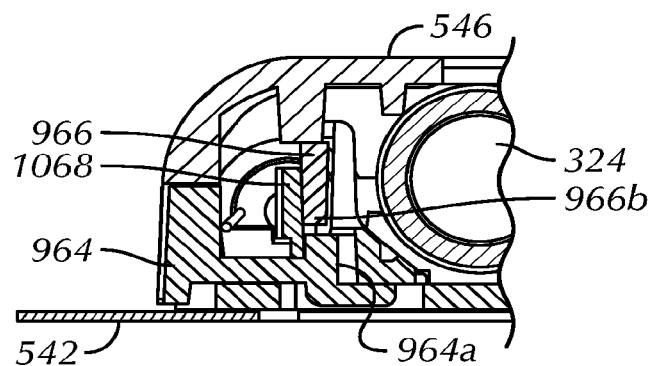
FIG. 12B is a partial, front, cross sectional view of the fluid delivery device shown in FIG. 12A taken along line 12B-12B.
Figure 13A:
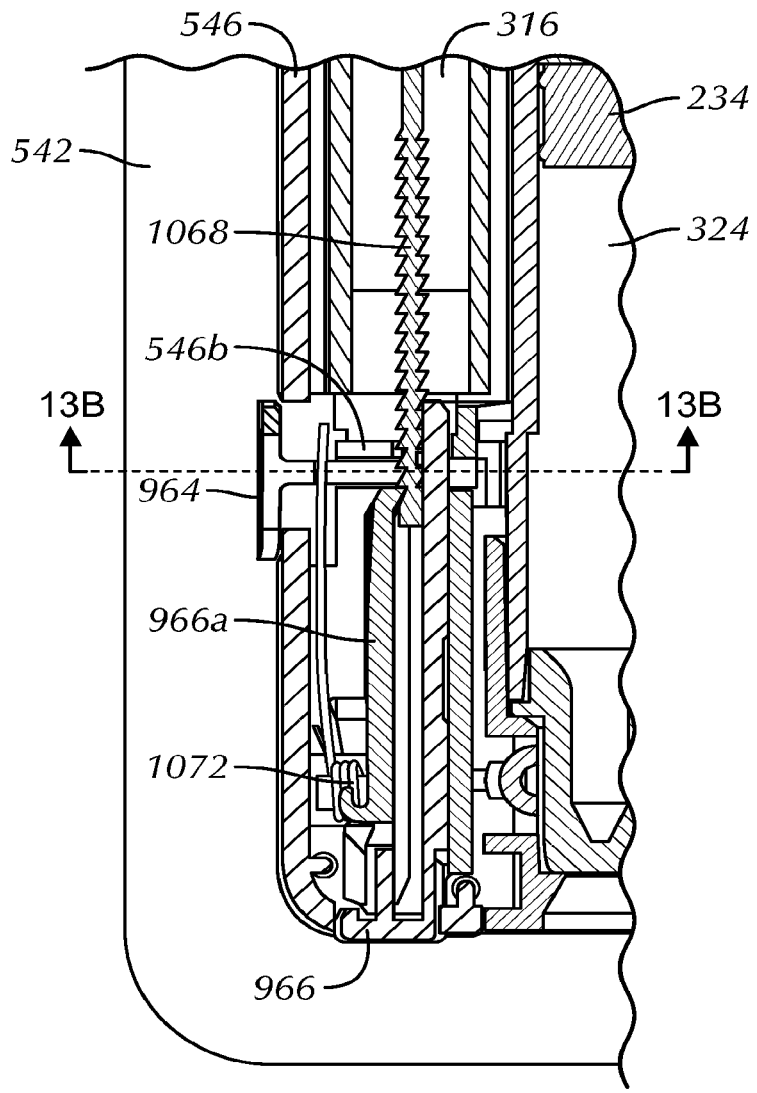
FIG. 13A is a partial, top, cross sectional view of the fluid delivery device shown in FIG. 1 taken along line 4A-4A with the bolus button in the locked position and a release button in a locked position and indicating that the bolus button has been completely deployed.
Figure 13B:
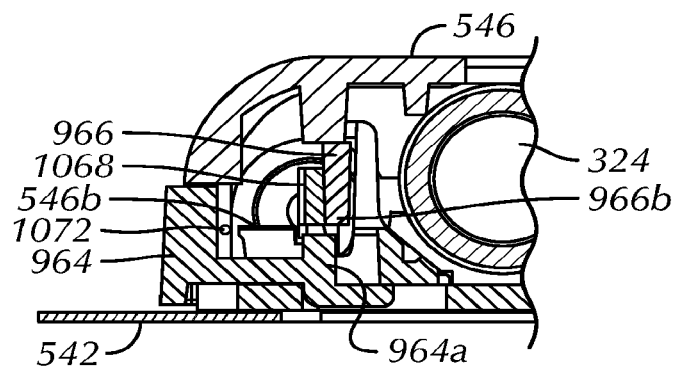
FIG. 13B is a partial, front, cross sectional view of the fluid delivery device shown in FIG. 13A taken along line 13B-13B.

Referring to FIG. 10B, the bolus release button 964 may engage with the bolus button 966 to control when the bolus button 966 is reset. In one embodiment, the bolus release button 964 includes a projection 964a that engages the bolus button 966 by selectively sliding through and being positioned within aperture 966b of the bolus button 966 (shown best in FIG. 2). In one embodiment, when the projection 964a of the bolus release button 964 is within the aperture 966b (as shown in FIGS. 10B, 12B and 13B) bolus button 966 on either end of the aperture 966b abuts against the projection 964a and prevents movement of the bolus button 966 in either direction. In one embodiment, depressing the bolus button 966 moves the projection 964a out of the aperture 966b and allows the bolus button 966 to be reset by the spring bias (as shown in FIG. 11B). In one embodiment, the bolus release button 966 is spring biased such that releasing the bolus release button 966 after depressing the bolus release button 966 biases the projection 964a against the side of the bolus release button 964 adjacent to the aperture 966b and such that once the aperture aligns with the projection 964a upon depressing the bolus button 966 the projection 964a immediately mates with the aperture 966b. In one embodiment, the bolus button 966 is spring biased with a torsion spring 1072. In one embodiment, the same torsion spring 1072 that biases the bolus button 966 spring biases the bolus release button 964.

FIGS. 10A-13B depict an exemplary sequence of events in bolus dosing. FIGS. 10A and 10B depict the position of the bolus button 966 and bolus release button 964 prior to bolus dosing; the bolus release button 964 is in the enabled position, and the bolus button 966 is locked in the depressed position. FIGS. 11A-11B depict the enabling step; the user depresses the bolus release button 964 to its stop position, causing the bolus button 966 to move to the extended position. The bolus button 966 is now enabled for one incremental dose. FIGS. 12A-12B illustrate delivery of a bolus dose; the user depresses the bolus button 966 to the stop position, causing the bolus actuator 322 to advance one increment, displacing the second moveable barrier 232 and dispensing one bolus dose. The bolus release button 964 is returned to the enabled position. FIGS. 13A-13B illustrate delivery of the last bolus dose of the device; the user depresses the bolus button 966 to its stop position, causing the bolus actuator 322 to advance one increment, displacing the second moveable barrier 232 and dispensing the final bolus dose. This activates a lock-out feature of the fluid delivery device 110, causing the bolus release button 964 to slide through an aperture 1068a (see FIG. 8) in the rack 1068 to the lock-out position. In one embodiment, once the bolus release button 964 extends outwardly through aperture 1068a, the torsion spring 1072 slides off a ledge 546b of the housing 546 and extends between the bolus release button 964 and the ledge 546b to retain the bolus release button 964 in the lock-out position (See FIG. 13B). The bolus release button 964 may be locked in place to prevent subsequent operation and to indicate to the user that all of the bolus doses have been delivered.

In one embodiment, the bolus button 966 remains in the depressed position slightly proud of (i.e. raised, projecting or extending from) the outer device surface of the housing 546. As a result of the user's pressing the bolus release button 964, the bolus actuator 322 may engage one bolus increment as the bolus button 966 extends further from the housing 546. When the user then depresses the bolus button 966 back to its original position (i.e., slightly proud of the housing 546), the bolus actuator 322 advances the second moveable barrier 232 a fixed amount or increment. The resulting movement of the second moveable barrier 232 displaces the hydraulic fluid and in turn displaces the third movable barrier 234 by essentially the same volume increment, dispensing a bolus dose of fluid from the fluid delivery device 110.

The second moveable barrier 232 may be capable of maintaining a seal as it translates within the hydraulic bolus chamber 316. In one embodiment, the second moveable barrier 232 is displaced by the rack 1068 by the distance equal to one ratchet spacing at a time per activation of the bolus button 966.

Figure 14:
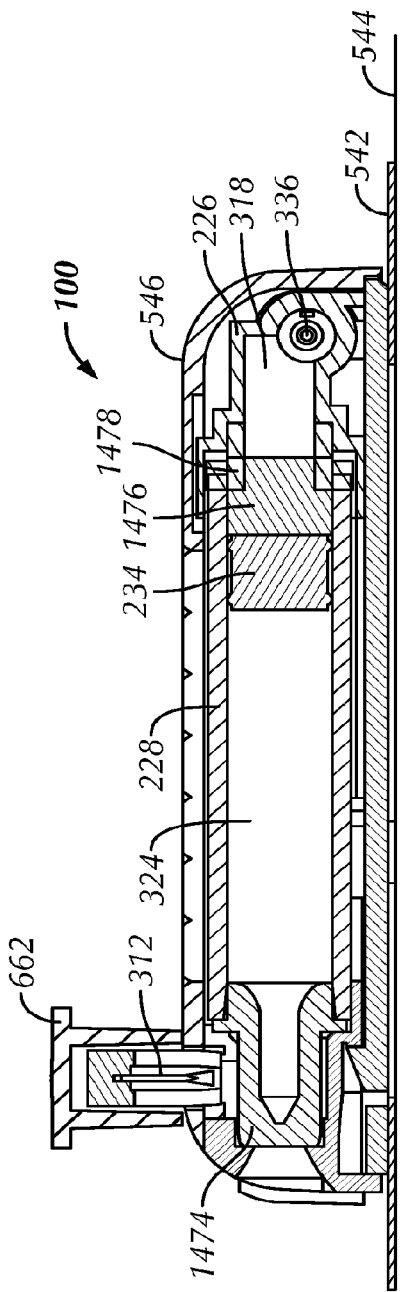
FIG. 14 is a side cross sectional view of a pump chamber, medicinal piston and a fluid reservoir of the fluid delivery device shown in FIG. 1 taken along line 14-14.

Referring to FIG. 14, in one embodiment, the fluid reservoir 324 initially is filled with a quantity of the fluid to be delivered to the user. In another embodiment, the fluid reservoir 324 may be filled by the user prior to use. In one embodiment, the fluid cartridge 228 of the fluid reservoir 324 is comprised of a rigid material. In one embodiment, the fluid cartridge 228 is comprised of Topas 6017 S-04. In some embodiments, the fluid cartridge 228 may be comprised of a polymer due to the reduce length of time of exposure of the fluid to the fluid cartridge 228 (for example, 24 hours after the user fills the fluid cartridge 228 and uses it) where previous fluid cartridges had to be comprised of a glass or other material having lower leachable and extractible properties for storage of the fluid over an extended period of time. Additionally, because known delivery devices include electronics, such devices are not practical for one day disposable use as is a purely mechanical device as disclosed in certain embodiments of the fluid delivery device 110 herein.

In the case of a medicament, the quantity of fluid may be pre-determined by a medical professional in order to provide the necessary dosing over a pre-determined period of time. The volume of the fluid reservoir 324 may be about 100 µl, 500 µl, 1 ml, 3 ml, 5 ml, 10 ml, 30 ml, 50 ml, 100 ml or more. The fluid cartridge 228 may include a septum 1474 within the distal end of the fluid cartridge 228. In one embodiment, the septum 1474 acts as a stopper. In other embodiments, the septum 1474 may be at least portion of the sidewall (not shown). In one embodiment, the fluid cartridge 228 includes a spacer 1476 on the hydraulic fluid side of the third moveable barrier 234 such that the size of the fluid cartridge 228 may adapt to a range of fluid volumes by varying the size of the spacer 1476. In one embodiment, the space 1476 may be brightly colored to help indicate the level of fluid within the fluid cartridge 228. The fluid cartridge 228 may include a seal 1478 that has an opening 1478a (see FIG. 2) such that the seal 1478 seals the fluid cartridge 228 to the manifold 226 while allowing the hydraulic fluid to pass through to either the spacer 1476 and/or the third moveable barrier 234.

In one embodiment, the septum 1474 is composed of a flexible material such as rubber and fits within fluid cartridge 228, forming a seal on the end opposite the third moveable barrier 234. The septum 1474 may be a hollow cylinder open only at the end that is installed in the fluid cartridge 228. The septum may remain stationary and is positioned to align with the needle 312. When the needle 312 pierces the side the septum 1474, the fluid path between the fluid delivery device 110 and the outside environment is opened, allowing the fluid to flow from the fluid delivery device 110. In one embodiment, the septum 1474 is exposed through a side of the housing 546 to allow for the user to fill the fluid reservoir 324. The septum 1474 may have a hardness sufficient to allow the needle 312 to move relative to the remainder of the fluid delivery device 110 as described in further detail below. In one embodiment, the septum 1474 has a hardness of 50 shore A.

Figure 15:
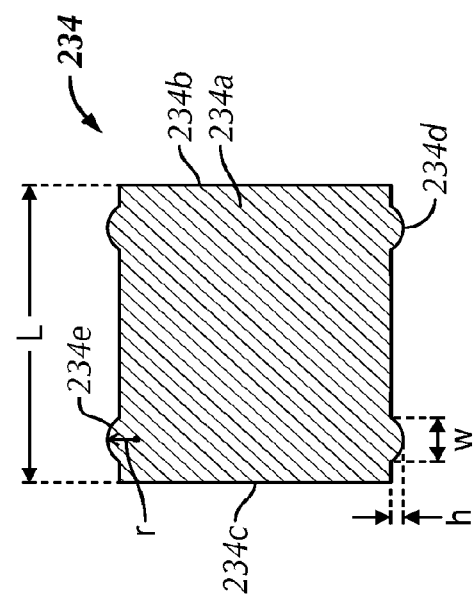
FIG. 15 is an enlarged side cross sectional view of the medicinal piston shown in FIG. 14.

Referring to FIG. 15, the third moveable barrier 234 may be a plunger that slides within the fluid cartridge 228. Typically, pistons may have imprecise sizing and compressibility characteristics because the impact on the delivery rate is not critical. In one embodiment, the third moveable barrier 234 of the fluid delivery device 110 however, is configured to minimize any impact on the fluid delivery rate. In one embodiment, the third moveable barrier 234 is comprised of a flexible material to form a seal between the hydraulic fluid and the fluid to be delivered to the user. In one embodiment, the third moveable barrier 234 has a similar configuration to the second moveable barrier 232. In one embodiment, the axial compressibility is minimized. In one embodiment, the axial compressibility of the second and third moveable barriers 232, 234 may be greater than the axial compressibility of the first moveable barrier 230 due to the lower pressure differentials acting on the second and third moveable barriers 232, 234. In such an embodiment, the lower axial compressibility allows for a thickness or length L that is greater than the thickness t of the first moveable barrier 230 and allows two points of contact. In one embodiment, the third moveable barrier 234 is comprised of a single material having a durometer between approximately 35 and approximately 65 shore A. In one embodiment, the durometer of the third moveable barrier 234 is between approximately 35 and approximately 65 shore A for a fluid cartridge 228 comprised of a polymer. In another embodiment, the durometer of the third moveable barrier 234 is between approximately 35 and approximately 45 shore A for a fluid cartridge 228 comprised of glass. In one embodiment, the durometer of the third moveable barrier 234 is 55 shore A with a fluid cartridge 228 comprised of a polymer. In one embodiment, the third moveable barrier 234 is comprised of Butyl Rubber. In one embodiment, the third moveable barrier 234 is coated with 0.0001 inch parylene C. In one embodiment, the third moveable barrier 234 has a minor diameter of approximately 0.2425 inches and a major diameter of approximately 0.2615 inches±0.002 inches.

In one embodiment, the third moveable barrier 234 includes a body 234a having a first end 234b and a second end 234c. The third moveable barrier 234 may include a first flange 234d and a second flange 234e. In one embodiment, the first and second flanges 234d, 234e are integral with the body 234a and extend radially outwardly from the body 234a proximate the first end and second ends 234b, 234c respectively, in an uncompressed state. The first and second flanges 234d, 234e may be configured such that contact with the fluid cartridge 228 is minimized. Having the first and second flanges 234d, 234e be integral with the body 234a may prevent roll over and flash points that occur with the use of separate o-rings. In one embodiment, the first and second flanges 234d, 234e have a curved cross sectional periphery in the uncompressed state. In one embodiment, the curve has a substantially constant radius r in the uncompressed state. In one embodiment, the first and second flanges 234d, 234e are spaced from the first and second ends 234b, 234c respectively in order to provide proper support for the first and second flanges 234d, 234e.

In one embodiment, control of the contact area of third moveable barrier 234 to the inner wall of the fluid cartridge 228 is addressed by the structural design of the first and second flanges 234d, 234e. In one embodiment, the first and second flanges 234d, 234e have a circular side cross sectional profile. In this embodiment a circular profile on the outer surface of a plunger constructed of an elastomeric material presents a small contact area that can be deformed with a minimal change in force. Though individual pistons and cylinders vary in size due to manufacturing tolerances, the contact area variation is reduced by the configurations disclosed herein. Providing two flanges provides redundant sealing to insure the isolation of the fluid from the hydraulic fluid.

In additional embodiments, the coefficient of friction between the third moveable barrier 234 and the fluid reservoir 324 is controlled by appropriate selection of contact materials. In this embodiment, one or more suitable coating agents are applied to the outer surface of the third moveable barrier 234 and/or the inner surface of the fluid reservoir 324 to minimize both the coefficient of friction and the variation of the coefficient of friction from device to device. In addition, a coating process using Parylene 'C' material may be used. A film coating with Parylene 'C' material greater than about 0.0001 inch (2.5 microns) has proven to contribute to controlling the movement of the third moveable barrier 234. The Parylene coating is preferably conformal and of uniform thickness and is substantially free of any voids or pinholes. Parylene may be applied at the molecular level by a vacuum deposition process at ambient temperature. Film coatings from about 0.100 to 76 microns are possible in a single operation. In one embodiment, no catalysts or solvents are required, and no foreign substances are introduced that could degrade the coated surface. Parylene 'C' is a modified version of Parylene which may provide a better combination of electrical and physical properties including low moisture and gas permeability.

Figure 16A:
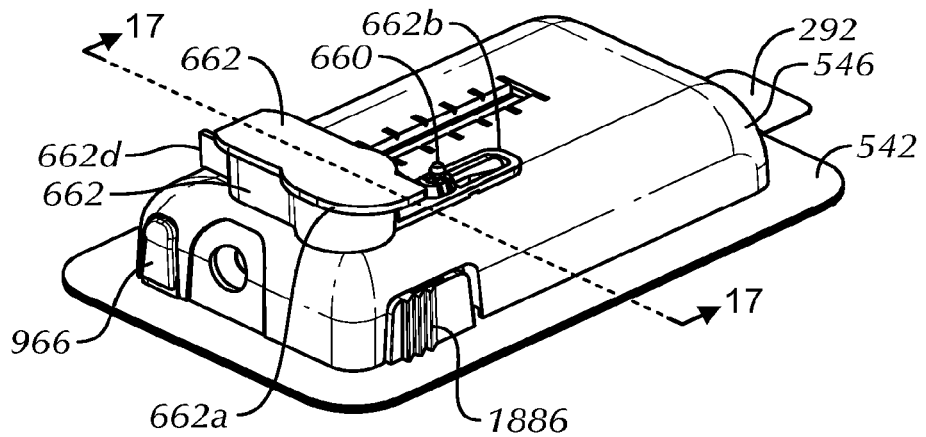
FIG. 16A is a perspective view of the fluid delivery device shown in FIG. 1 in an initial or storage position.
Figure 16B:
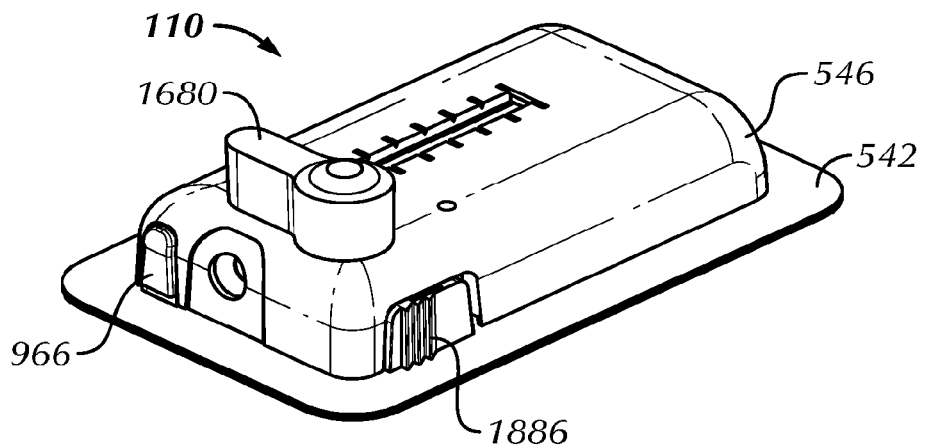
FIG. 16B is a perspective view of the fluid delivery device shown in FIG. 1 with the button cap removed and the biasing members engaged.
Figure 16C:
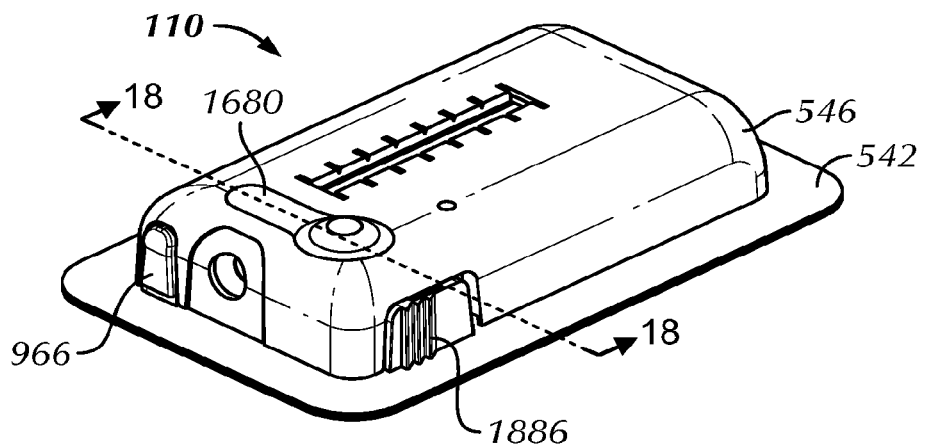
FIG. 16C is a perspective view of the fluid delivery device shown in FIG. 1 in the engaged position.

Referring to FIGS. 16A-16C, in one embodiment, the fluid delivery device 110 has multiple operable states. In a first operable state or storage position (FIG. 16A), the needle 312 is not engaged or is separated from the fluid reservoir 324 and does not extend from the housing 546 (i.e. not inserted into the body). In a second operable state or engageable position (FIG. 16B), the needle 312 is able to be engaged with the fluid reservoir 324. In a third operable state or engaged or activated position (FIG. 16C), the needle 312 is in fluid communication with the fluid to be delivered and is inserted into the body or available for insertion into the body. In a fourth operable state or disengaged or disposable position (not shown), the needle 312 is again separated from the fluid to be delivered, is not inserted into the body, and is fixedly retained (locked) within the housing 546.

In one embodiment, the button cover 662 shrouds the needle 312 preventing accidental depression of the needle 312 during handling and shipping of the fluid delivery device 110. In one embodiment, the button cover 662 includes a flange 662a to facilitate grasping and removing the button cover 662 by the user. In one embodiment, the button cover 662 has a projection 662b for coupling with the pin 660. The button cover 662 may include indicia 662c such as the word "Remove" to indicate what the user should do with the button cover 662 (See FIG. 2). In one embodiment, the button cover 662 includes a tab 662d for providing leverage against the housing 546 as the button cover 662 is removed by holding the flange 662a on the opposite side of the button cover 662. In one embodiment, when the button cover 662 is removed, a needle button 1680 coupled to the needle 312 is exposed (FIG. 16B).

Figure 19:
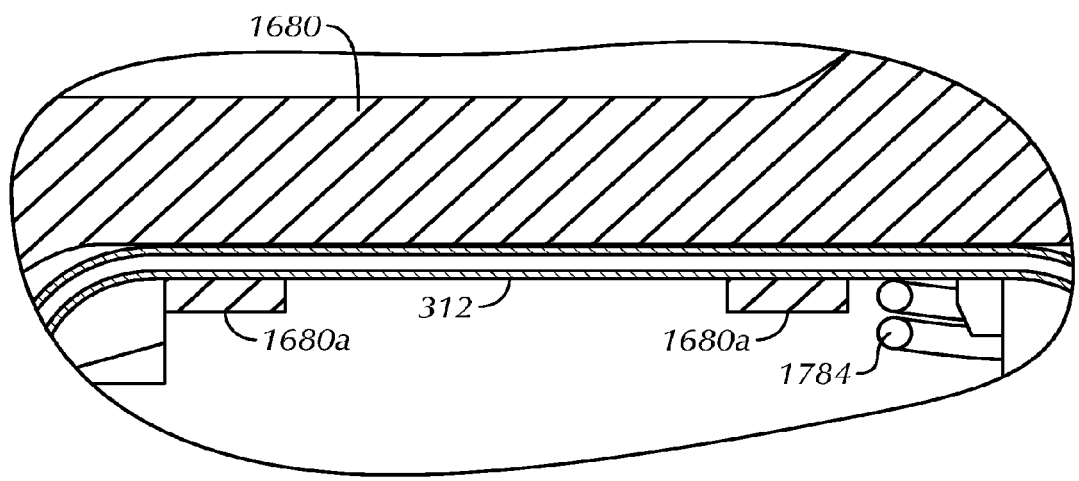
FIG. 19 is an enlarged front cross sectional view of a portion of a needle with a needle cap shown in FIG. 18.

In one embodiment, the needle 312 is fixed to the needle button 1680. In one embodiment, the needle 312 is heat staked to the needle button 1680 at points 1680a as shown in FIG. 19. In other embodiments, the needle 312 is moveable relative to the needle button 1680. In one embodiment, removal of the button cover 662 simultaneously removes the pin 660 from the basal actuator 320 to release or activate the basal actuator 320 such that it acts on the hydraulic fluid.

Thus, in preferred embodiments, the button cover 662 performs the dual functions of shrouding and protecting the needle button 1680 to prevent unintentional activation of the needle 312 and simultaneously controls activation of the basal actuator 320.

Figure 17:
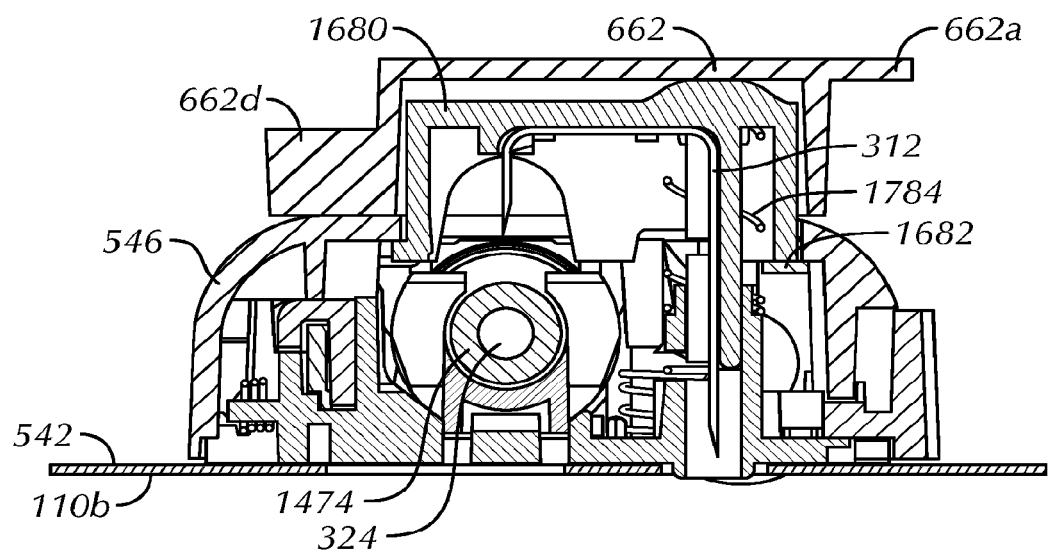
FIG. 17 is a front cross sectional view of the fluid delivery device shown in FIG. 16A taken along line 17-17.
Figure 18:
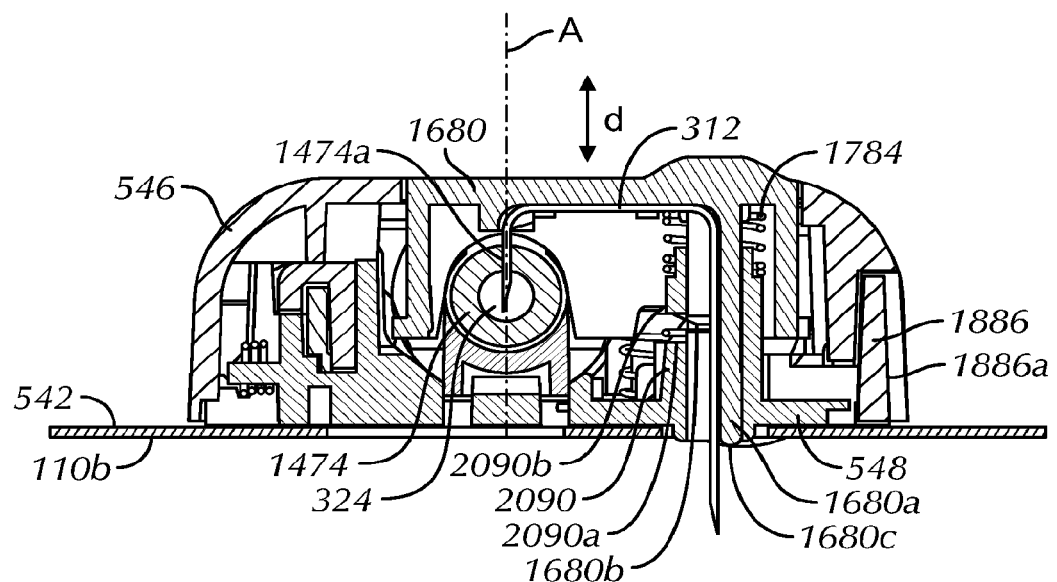
FIG. 18 is a front cross sectional view of the fluid delivery device shown in FIG. 16C taken along line 18-18.

Referring to FIGS. 17 and 18, in one embodiment, the needle button 1680 deploys the needle 312 when depressed (FIG. 18). The needle button 1680 may be spring biased away from the septum 1474. In one embodiment, the needle button 1680 is spring biased by a compression spring 1784 as described further below. A first force may be required to move the needle button 1680 from the initial position. In one embodiment, the first force is greater than a second force that is required to move the needle button 1680 the remainder of way (i.e. at least greater than the force from the spring 1784) to the engaged position to help users overcome the fear of depressing the needle 312 into the skin surface 544. In one embodiment, one or more breakable tabs 1682 extend from the housing 546 such that the tabs 1682 break upon providing the first force in the first direction d such that the user completes the deployment or insertion of the needle 312 quickly and fully after the tabs 1682 release the needle button 1680 and helps to prevent failed or partial insertion or engagement attempts. In the deployable position, the needle 312 may be moveable nearly exclusively in the engagement direction (i.e. toward the septum 1474) such that the needle 312 enters the septum and the user with little to no movement in the transverse direction to help ensure proper engagement. Once the needle 312 is in the engaged position, the needle 312 may then move relative to the remainder of the fluid delivery device 110 to reduce pain caused by movement of the needle 312 relative to the user as described below. In one embodiment, the needle 312 is flexible and restraining movement of the needle 312 during engagement aids in proper engagement of the needle 312.

In one embodiment, the needle 312 extends from the fluid reservoir 324, through the pierceable member or septum 1474 at a connection point 1474a and out of the housing 546. The needle 312 may be moveable relative to the septum 1474 or the fluid delivery device 110 may move relative to the needle 312 such that when the needle 312 extends into the skin surface 544 in the engaged position, movement of the needle 312 relative to the user caused by movement of the fluid delivery device 110 is reduced. Minimizing the movement of the needle 312 relative to the user may help to reduce pain or "pinching" caused by the needle 312.

In one embodiment, the needle 312 is configured to translate in a direction perpendicular to the septum 1474, e.g. direction d in FIG. 18, and pivot about the connection point 1474a in all directions. In one embodiment, the pivot of the needle 312 about the connection point 1474a is within the boundaries of an imaginary hour glass shaped path (not shown) proximate the septum 1474. In one embodiment, the entire needle 312 is configured to pivot about the connection point 1474a due to the flexibility of the septum 1474 and is limited by the connection between the needle button 1680 and the housing 546. In one embodiment, the needle 312 is configured to be entirely within or at least shrouded by the housing 546 and disengaged from the fluid reservoir 324 in an initial position (FIG. 17) and fluidly coupled with the fluid reservoir 324 and extending from the housing 546 in an engaged position (FIG. 18). In one embodiment, the needle 312 is configured to pierce the pierceable member 1474 after extending from the housing 546 when moving the needle 312 from the initial position to the engaged position such that the fluid does not exit onto the skin surface 544 and interfere with the adhesion of the adhesive patch 542. In one embodiment, the needle 312 is configured such that the needle 312 pierces the skin surface 544 approximately simultaneously to when the needle 312 pierces the pierceable member 1474.

In one embodiment, the needle 312 is generally J-shaped such that its two ends are pointing in the same direction but are axially and laterally spaced from one another. In one embodiment, the needle 312 includes two generally perpendicular bends with one end of the needle 312 being shorter than the other. In one embodiment, the septum 1474, or at least a surface tangent to the connection point 1474a, is generally parallel to a bottom surface 110b of the housing from which the needle 312 extends in the engaged position. In one embodiment, the needle 312 is a microneedle. In one embodiment, the needle 312 is a fine gauge needle. In one embodiment, the needle 312 is a 30 gauge needle. In one embodiment, both ends of the needle 312 are beveled to help facilitate piercing of the septum 1474 and the skin surface 544. In one embodiment, the needle 312 is configured to rotate about an imaginary axis A that extends through the connection point 1474a perpendicular to the septum 1474 as shown in FIG. 18 such that the fluid delivery device may rotate about the axis A without, or at least reduces, the end of the needle 312 extending into the user moving in an arched path.

In one embodiment, once the needle 312 is in the engaged position the needle button 1680 is locked into place and the fluid in the fluid reservoir is in liquid communication with the outside environment (e.g., the body) via the needle 312. The locking member 2088 may be configured to keep the first and second ends of the needle 312 disengaged from the user and the fluid reservoir 324 and contained within the housing 546 in a locked position upon moving the needle from the engaged position (FIG. 18) to the locked position (FIG. 23). In the locked position, the needle 312 may be kept from redeployment or engagement such that the housing 546 acts as its own sharps container. In one embodiment, the needle 312 is moved to the locked position through use of a needle release or lock button 1886.

Figure 20:
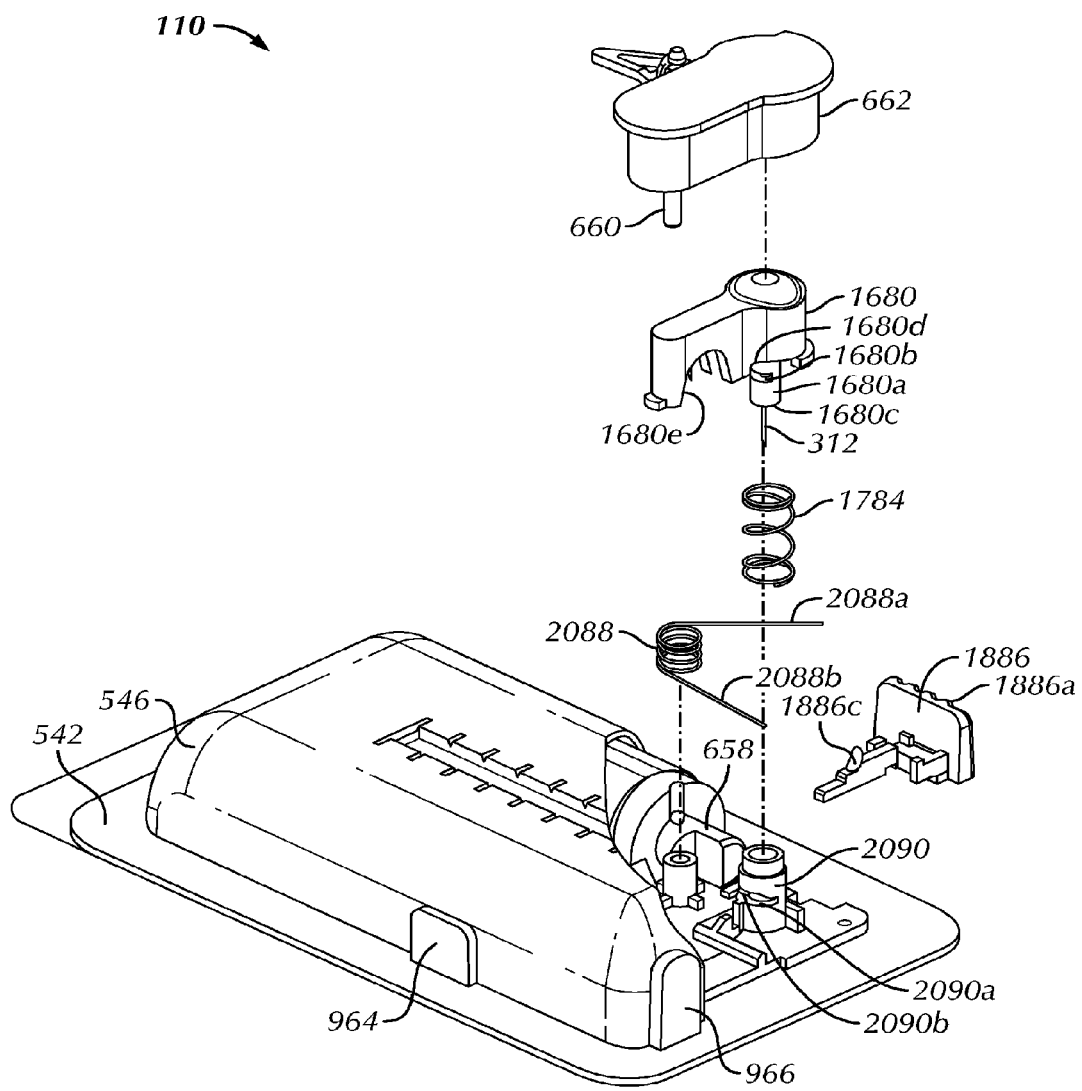
FIG. 20 is a partially exploded cut away view of a lock out assembly of the fluid delivery device of FIG. 1.
Figure 21:
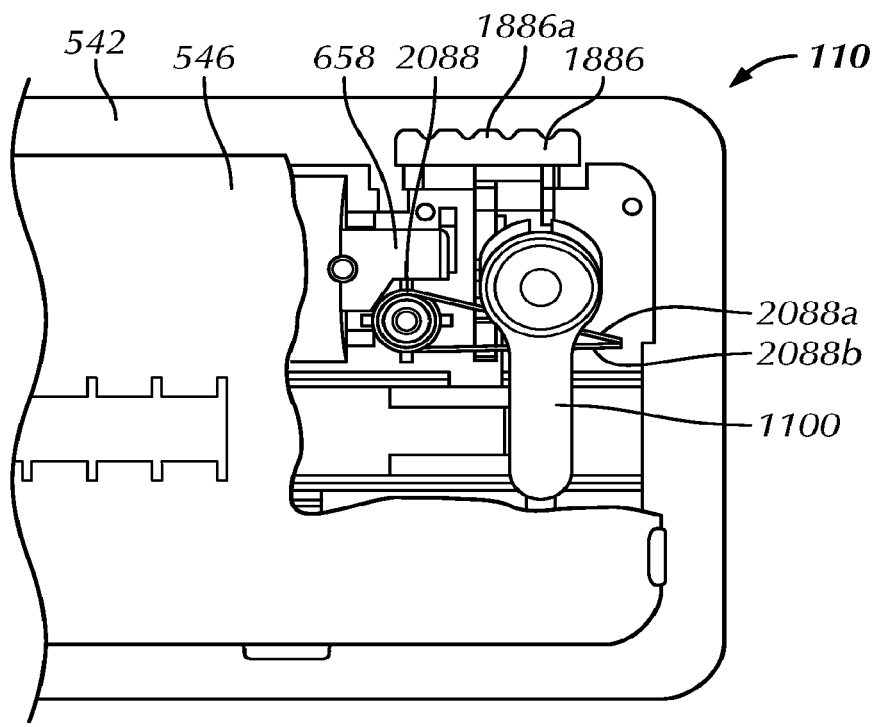
FIG. 21 is a top, partially cut away view of a lock out assembly of the fluid delivery device of FIG. 1 in an initial or ready to be engaged position.

Referring to FIG. 20, in certain embodiments, the spring 1784 is located between the needle button 1680 and the base 548 and surrounds a boss or sleeve 1680a of the needle button 1680 extending partially over the needle 312. In one embodiment, the spring 1784 becomes compressed when needle button 1680 is locked in the depressed, engaged or inserted position (FIG. 18) to bias the needle button 1680 away from the septum 1474. The needle button 1680 may be retained in the inserted position by a locking member as described further below. The locking member 2088 may be released when the user is finished with the fluid delivery device 110. In one embodiment, prior to removing the fluid delivery device 110 from the body, the user activates the lock button 1886 to retract the needle 312 from the user and into the housing 546. In other embodiments, the needle 312 is automatically retracted after the fluid reservoir 324 is substantially empty or automatically upon removal of the fluid delivery device 110 from the skin surface 544.

Figure 22:
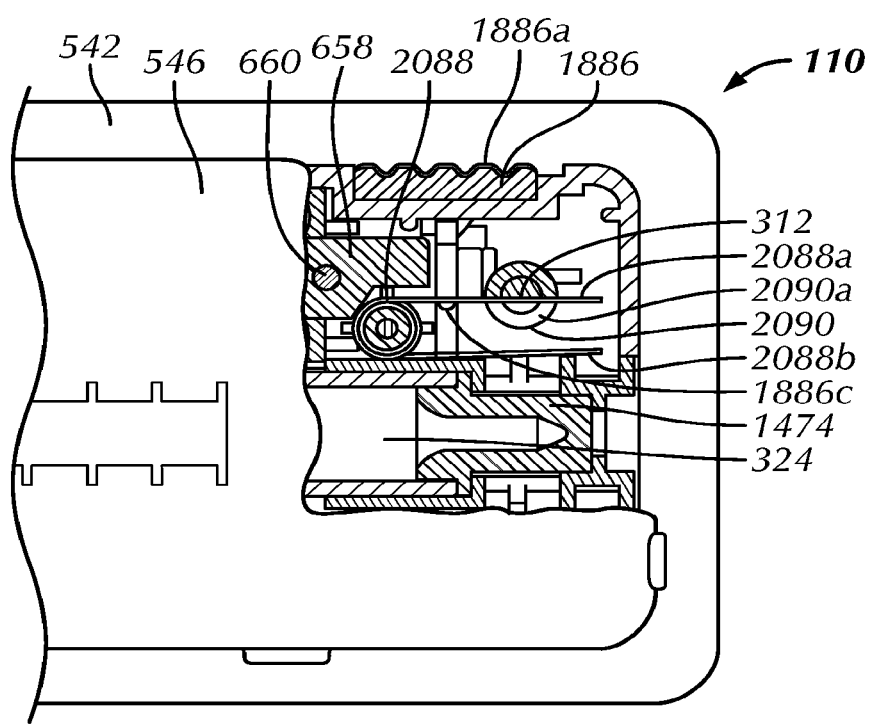
FIG. 22 is a top, partially cut away view of a lock out assembly of the fluid delivery device shown in FIG. 1 in a locked out position.

In one embodiment, the locking member 2088 is a spring. In one embodiment, the locking member 2088 is comprised of a helical torsion spring. In one embodiment, the locking member 2088 biases the lock button 1886 and interacts with features of the needle button 1680 and the base 548 to releaseably retain the needle 312 in the depressed or inserted position (FIG. 18) and unreleaseably locked in the lock-out position (FIG. 22).

In one embodiment, the locking member 2088 is coupled to or engageable with the lock button 1886. In one embodiment, the lock button 1886 has a surface 1886*a* exposed through the housing 546. In one embodiment, the surface 1886*a* of the lock button 1886 is exposed through an aperture in the housing 546 on a first side of the housing 546 and the housing 546 has a surface on a second side of the housing 546 opposed to the first side of the housing and generally aligned with the lock button 1886 such that the user can grip the lock button 1886 and the housing 546 between a thumb and a finger to activate the lock button 1886 within engaging the bolus release button 964 preventing accidental activation of the lock button 1886 when using the bolus actuator 322. The lock button 1886 may include at last one projection 1886*b* extending from the surface to help facilitate grip with the user's hand. In one embodiment, the at least one projection 1886*b* is ramped (see FIG. 23A) to further facilitate grip and help indicate to the user by feel which direction the lock button 1886 should be urged.

Referring to FIG. 20, in one embodiment, the sleeve 1680*a* surrounds the needle 312 and the locking member 2088 is spring biased toward the sleeve 1680*a*. In one embodiment, the sleeve 1680*a* has at least one abutment surface configured to engage with the locking member 2088 to prevent at least one of engaging and disengaging the needle 312. In one embodiment, the at least one abutment surface includes a first abutment surface 1680*b* and a second abutment surface 1680*b*.

In one embodiment, the first abutment surface 1680*b* is axially spaced along the needle 312 from the second abutment surface 1680*c*. In one embodiment, the first abutment surface 1680*b* is a radially inwardly extending groove. In one embodiment, the second abutment surface 1680*c* is the distal end of the sleeve 1680. In other embodiments, the first and second abutment surfaces 1680*b*, 1680*c* are any surface such as a projection or groove that axially engages with the locking member 2088. In one embodiment, the base 548 includes an upwardly extending boss or guide 2090 for receiving and guiding the sleeve 1680*a* and engaging with the locking member 2088. In one embodiment, the guide 2090 loosely fits over the sleeve 1680*a* to allow some non-axial movement or pivot of the needle button 1680 relative to the base 2090 for the pivoting of the needle 312 as described above. The guide 2090 may include a groove 2090*a* configured to receive the locking member 2088. In one embodiment, the groove 2090*a* aligns with the first abutment surface 1680*a* in the engaged position (FIG. 18) and aligns with the second abutment surface 1680*b* in the locked-out position (FIG. 22). In one embodiment, the locking member 2088 engages with the first abutment surface 1680*b* to releaseably retain the needle 312 in the engaged position (FIG. 18) and locking member 2088 engages with the second abutment surface 1680*c* to unreleaseably retain the needle 312 in the locked position (FIG. 22). In one embodiment, the lock button 1886 is configured to position the locking member 2088 into the locked position upon disengaging the needle 312 from the user.

Referring to FIG. 20, in one embodiment, the locking member 2088 is configured to provide an audible feedback upon retaining the needle 312 in the engaged position so the user is assured that the needle 312 has been fully deployed and in the engaged position. In one embodiment, the guide 2090 includes a projection 2090*b* that facilitates creating an audible "click" by sliding the locking member 2088 over and into the groove 2090*a* and first abutment surface 1680*a*. In one embodiment, the projection 2090*b* is a ramped surface 1886*c* that is selectably engageable with the locking member 2088. In one embodiment, the locking member 2088 is biased against the guide 2090 above the groove 2090*a* (see FIG. 21) and depressing the needle button 1680 engages a surface 1680*d* with the locking member 2088 and slides the locking member 2088 down the guide 2090 over the projection 2090*b* and into the aligned groove 2090*a* and first abutment surface 1680*a*. In one embodiment, the needle button 1680 includes a cutout 1680*e* to fit over the septum 1474. In one embodiment, the cutout 1680*e* is loosely sized to the contour of the septum 1474 to support the needle 312 relative to the housing 546 but allows for the movement of the needle 312 described above.

In one embodiment, when the user depresses the needle button 1680, a free end or first arm 2088*a* of the locking member 2088 is moved from its initial preloaded position against the guide 2090 and into the aligned groove 2090*a* and first abutment surface 1680*a*. When the lock button 1886 is depressed the ramped surface 1886*c* may force the first arm 2088*a* of the locking member 2088 from the first abutment surface 1680*a* momentarily, allowing needle button 1680 to retract to the upright or initial position as a result of the force from the spring 1784. As the user continues to press the lock button 1886, the end of the first arm 2088*a* may abut a surface within the housing 546, preventing further rotation (similar to the position shown in FIG. 21). The mid section of the first arm may then deflect over the ramped surface 1886*c* of the lock button 1886 allowing the first arm 2088*a* to spring back into the groove 2090*a* (FIG. 22). The second abutment surface 1680*c* of the needle button 1680 may then be axially above the first arm 2088*a* extending across the guide 2090 preventing the needle button 1680 and needle 312 from further translation or re-depression/re-deployment (FIG. 22).

Figure 23A:
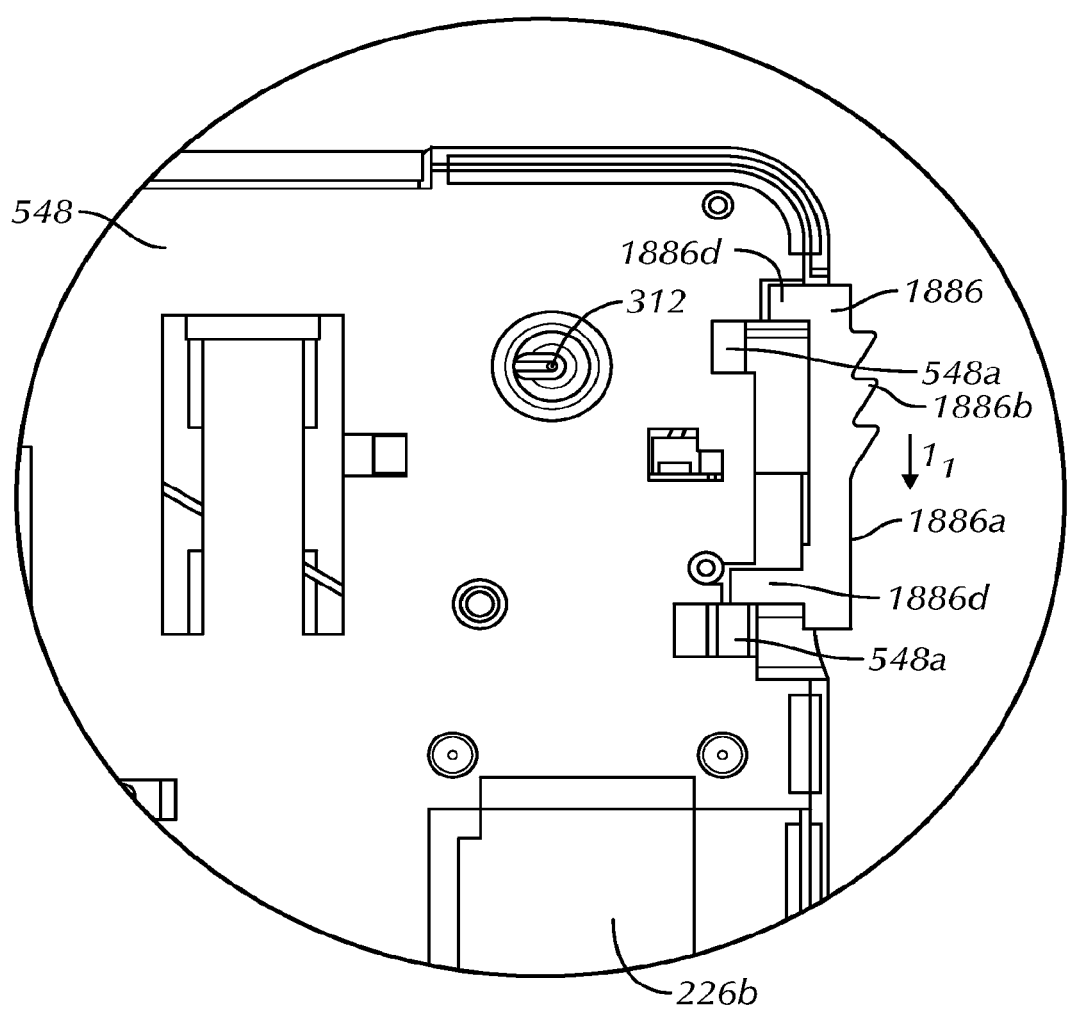
FIG. 23A is a partial bottom plan view of the fluid delivery device of FIG. 1 with the adhesive patch removed showing a lock button in an initial position.
Figure 23B:
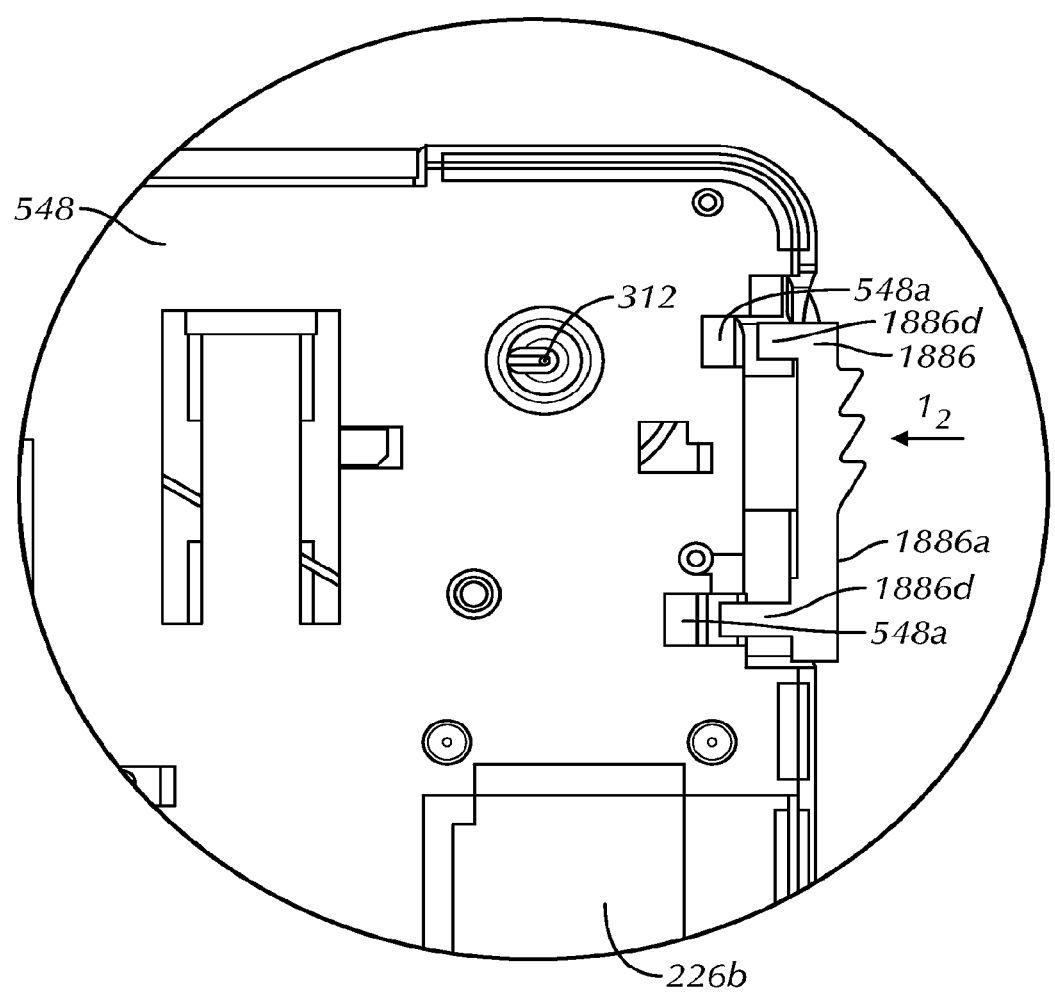
FIG. 23B is a partial bottom plan view of the fluid delivery device shown in FIG. 23A with the lock button moved in a first direction.
Figure 23C:
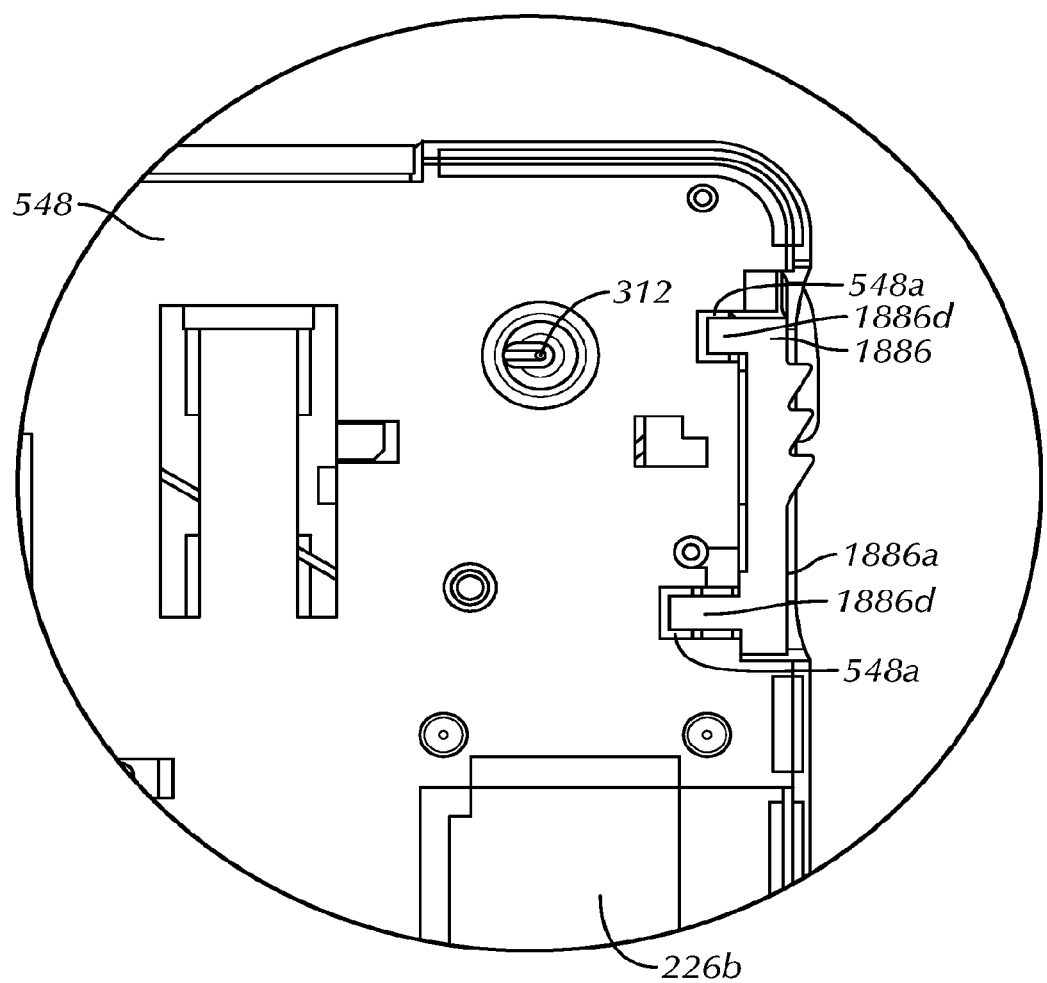
FIG. 23C is a partial bottom plan view of the fluid delivery device shown in FIG. 23A with the lock button moved in first and second directions.

Referring to FIGS. 23A-23C, in one embodiment, the lock button 1886 is configured to release the locking member 2088 only after completing two distinct motions to prevent accidental release of the locking member 2088. In one embodiment, the lock button 1886 is configured to move in a first direction $l_1$ and move in a second direction $l_2$ only after moving a predetermined distance in the first direction. In one embodiment, the lock button 1886 includes at least one projection 1886*d* and the housing or base 548 includes at least one slot 548*a* each configured to receive one of the at least one projection 1886*d*. In one embodiment, each at least one slot 548*a* is unaligned with one of the at least one projection 1886*d* in an initial position (FIG. 23A) and aligned with one of the at least one projection 1886*d* after moving the lock button 1886 the predetermined distance in the first direction $l_1$ (FIG. 23B) and each at least one slot 548*a* receiving one of the at least one projection 1886*d* after moving the lock button 1886 a predetermined distance in the second direction $l_2$. In one embodiment, the first and second directions $l_1$ and $l_2$ are linear translations. In one embodiment, the first direction is perpendicular to the second direction as shown in FIGS. 23A-23C. In other embodiments, the first and second directions are any directions such as curved and/or rotational. In one embodiment, the lock button 1886 is spring biased in a direction opposite the first direction. In one embodiment, the lock button 1886 is retained in the first direction by one or more breakaway tabs (not shown). In other embodiments, the lock button 1886 is comprised of more than one button.

Referring to FIG. 2, in some embodiments, the fluid delivery device 110 may include one or more view windows. View windows can be, for example, on the top side and/or the bottom side of the fluid delivery device 110. These view windows allow light penetration to facilitate point of care filling of the fluid reservoir 324, to increase viewability to determine level and viability of fluid, and to enhance user confidence by allowing observation by allowing the user to observe the relative position of the third moveable barrier 234 during delivery and/or filling. In one embodiment, the housing 546 includes a window 546a generally aligned with the fluid cartridge 228. In one embodiment, the adhesive patch 542 includes a window 542b. The window 542b may be a translucent area or simply a gap in the material. In one embodiment, the windows 542a and 542b are generally aligned. In one embodiment, the remainder of the exposed housing 546 is opaque such that only the fluid cartridge 228 is visible through the housing 546.

In some embodiments, the fluid delivery device 110 includes an adhesive to facilitate attachment of the fluid delivery device 110 to the skin surface 544 of the user (see e.g. FIG. 9A). The adhesive strength should preferably be sufficient to adhere the fluid delivery device 110 to the skin surface 544 of the user for the duration of treatment with the drug-filled fluid delivery device 110. Thus, adhesive strength may vary depending on the duration of treatment (e.g., 72 hours, 48 hours, 24 hours, 18 hours, 12 hours, etc.). Moreover, the adhesive should be such that the fluid delivery device 110 is easily removable without undue discomfort or pain or difficulty upon completion of use. In some embodiments, the adhesive may be relieved in certain areas, e.g., in the area of the hydraulic basal chamber 314 (see e.g. area 542a in FIG. 2), the fluid reservoir 324 (see e.g. area 542b in FIG. 2) and/or proximate the needle 312 (see e.g. area 542c in FIG. 2), to facilitate contact of the fluid delivery device 110 with the skin surface 544 of the user.

The adhesive may be combined with a pad to form an adhesive patch 542. In one embodiment, the adhesive patch 542 is a non-woven foam pad. In one embodiment, the adhesive patch 542 is comprised of a medical foam adhesive manufactured by 3M®. In one embodiment, the adhesive patch 542 is comprised of 3M® 9776 material. In one embodiment, the outer dimension of the adhesive patch 542 extends beyond the outer dimensions of the housing 546 to allow greater adhesive surface area and/or greater flexibility of the adhesive patch 546 to contour to the user's body shape. In certain embodiments, extended area is, for example, about 0.010 inches, 0.100 inches, 0.250 inches, 0.500 inches or more from the housing 546. The adhesive patch 542 may be capable of movement (e.g. flexing, stretching) in multiple orientations to improve comfort of wear and reduce pinching or tightness or the wearer's perception of pinching or tightness. In one embodiment, the adhesive is initially covered by a removable film 292 (see FIG. 2). In one embodiment, the film 292 includes a tab 292a extending outwardly from the adhesive patch 542 to facilitate removal from the adhesive patch 542 just prior to applying the fluid delivery device 110 to the skin surface 544.

Referring to FIGS. 16A-16B, in exemplary use, the user removes the fluid delivery device 110 from a storage package (not shown). The user may then fill the fluid cartridge 228 with the fluid. In one embodiment, the fluid cartridge 228 is pre-filled. Once the fluid cartridge 228 is filled, the user may remove the button cover 662 exposing the needle button 1680 and simultaneously activating the basal actuator 320. Referring to FIG. 9A, the user may then remove the film 292 from the adhesive patch 542 and place the fluid delivery device 110 on the skin surface 544. In other embodiments, the fluid delivery device 110 is placed on the skin surface 544 before removing the button cover 662. Once the fluid delivery device 110 is on the skin surface 544 and the button cover 662 is removed, the user may then depress the needle button 1680 to engage the needle 312 (see FIG. 18) and fluidly couple the user and the fluid reservoir 324. Once the needle 312 is engaged and when appropriate, the user may then activate the bolus release button 964 (FIG. 9A) and then activate the bolus button 966 (FIG. 9B) to deliver a bolus dosage. Once the delivery period (e.g. 24 hours) is complete or the user otherwise wants to remove the fluid delivery device 110, the user depresses the lock button 1886 (see FIGS. 23A-23C) to retract the needle 312 into the housing 546 (FIG. 22). Once the needle 312 is shrouded by the housing 546, the user may then remove the fluid delivery device 110 from the skin surface 544, dispose the fluid delivery device 110 and repeat the above steps to install a fresh fluid delivery device 110.

It will be appreciated by those skilled in the art that changes could be made to the exemplary embodiments shown and described above without departing from the broad inventive concept thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and features of the disclosed embodiments may be combined. The words "inwardly" and "outwardly" refer to directions toward and away from, respectively, the geometric center of the fluid delivery device. Unless specifically set forth herein, the terms "a", "an" and "the" are not limited to one element but instead should be read as meaning "at least one".

We claim:

1. A fluid delivery device comprising:
a housing configured to contain a fluid reservoir;
a needle configured to be in fluid communication with the fluid reservoir in an engaged position and out of fluid communication with the fluid reservoir in an armed position and a storage position;
a cap coupled to the housing and extending over a needle button coupled to the needle in the storage position and preventing the fluid delivery device from transitioning to the armed and engaged positions;
a biasing member having a proximal end coupled to the housing and a distal end configured to provide a force for the fluid reservoir; and
a plunger coupled to the distal end of the biasing member, the plunger being fixed with respect to the housing in the storage position such that the biasing member does not provide the force to the fluid reservoir and moveable with respect to the housing in the armed position such that the biasing member provides the force to the fluid reservoir,
wherein the cap includes a pin extending through the housing and releaseably retaining the plunger in the storage position such that removing the cap from covering the needle button releases the plunger from the housing and transitions the fluid delivery device from the storage position to the armed position.

2. The fluid delivery device of claim 1, further comprising a hydraulic basal chamber coupled between the biasing member and the fluid reservoir.

3. The fluid delivery device of claim 2, further comprising a hydraulic pump chamber and a flow restrictor fluidly coupling the hydraulic pump chamber and the hydraulic basal chamber.

4. The fluid delivery device of claim 2, wherein the plunger includes a plunger tip coupled to the hydraulic basal chamber.

5. The fluid delivery device of claim 1, wherein the biasing member comprises at least two overlapping coaxial springs.

6. The fluid delivery device of claim 1, wherein the plunger extends through the biasing member.

7. The fluid delivery device of claim 1, wherein the needle is not moveable relative to the fluid reservoir in the storage position and moveable relative to the fluid reservoir in the armed position.

8. The fluid delivery device of claim 1, wherein the housing contains
   a fluid reservoir.

9. The fluid delivery device of claim 1, wherein a delivery end of the needle is contained within the housing in the storage and armed positions and extends from the housing in the engaged position.

10. A fluid delivery device comprising:
   a housing configured to contain a fluid reservoir;
   a needle having a storage position, an armed position, and an engaged position, the needle configured to be in fluid communication with the fluid reservoir in the engaged position and out of fluid communication with the fluid reservoir in the armed and storage positions;
   a biasing member having a proximal end and a distal end, the proximal end of the biasing member being coupled to the housing and the distal end of the biasing member configured to provide a force for the fluid reservoir; and
   a plunger coupled to the distal end of the biasing member, the plunger being fixed with respect to the housing in a locked position such that the biasing member does not provide the force to the fluid reservoir and moveable with respect to the housing in a released position such that the biasing member provides the force to the fluid reservoir,
   wherein transitioning the needle from the storage position to the armed position transitions the plunger from the locked position to the released position,
   wherein the plunger is releaseably coupled to the housing with a pin extending through the housing and a cap extends over the needle in the storage position, the cap being coupled to the pin such that removing the cap releases the plunger from the housing.

\* \* \* \* \*